US005900427A

United States Patent [19]

Vedejs et al.

[11] Patent Number: 5,900,427

[45] Date of Patent: May 4, 1999

[54] N-HETEROARENESULFONYL-PROTECTED AMINO ACID REAGENTS FOR PEPTIDE SYNTHESIS

[75] Inventors: Edwin Vedejs; Jiabing Wang, both of Madison, Wis.; Shouzhong Lin, Arlington, Mass.; Artis Klapars, Madison, Wis.

[73] Assignee: Wisconsin Alumni Research Foundation, Madison, Wis.

[21] Appl. No.: 08/646,747

[22] Filed: May 3, 1996

[51] Int. Cl.[6] ........................ A61K 31/425; C07D 277/76

[52] U.S. Cl. .......................... 514/367; 514/376; 514/369; 514/375; 548/166; 548/221; 548/186; 548/229

[58] Field of Search .................................... 548/169, 166, 548/221; 514/367, 375

[56] References Cited

U.S. PATENT DOCUMENTS

| | | | |
|---|---|---|---|
| 4,069,259 | 1/1978 | Cipris et al. | 260/608 |
| 5,202,339 | 4/1993 | Mochida et al. | 514/327 |
| 5,240,923 | 8/1993 | Dean et al. | 514/226.5 |
| 5,258,361 | 11/1993 | Lopez | 504/273 |
| 5,276,025 | 1/1994 | Baldwin et al. | 514/211 |
| 5,430,006 | 7/1995 | Gesing et al. | 504/213 |
| 5,462,957 | 10/1995 | Niimura et al. | 514/397 |
| 5,470,853 | 11/1995 | Flaugh et al. | 514/232.8 |
| 5,510,491 | 4/1996 | Carpino et al. | 546/344 |

FOREIGN PATENT DOCUMENTS 430884 6/1991 European Pat. Off. .

OTHER PUBLICATIONS

Vedejs et al., J. Am. Chem. Soc., 118, 9796–97 (1996).
Stanovnik et al., Arch. Pharm. Ber. Dtsch. Pharm. Ges., 300(4), 322–25 (1967).
Banks et al., J. Appl. Chem., 18, 262–65 (1968).
du Vigneaud et al., *J. Am. Chem. Soc.* 76 (1954), 3113.
Kovacs et al. *J. Org. Chem.* 31 (1966) 119.
Rudigner et al., *Helv. Chim.* 56 (1973) 2216.
Kestemont, *Tetrahedron Lett.* 32 (1991) 1425.
Kemp et al., *Synthesis*, 32 (1988).
Fukuyama et al., *Tet. Lett.* 36 (1995) 6373.
Roblin et al., *J. Am. Chem. Soc.* 72 (1950) 4890.
Carpino et al., *J. Org. Chem.* 56 (1991) 2611.
El–Abadelah et al., *Heterocyles* 32 (1991) 1879.
Vedejs et al., *J. Am. Chem. Soc.* 115 (1993) 1607.
Shankar et al., *J. Heterocyclic Chem.*, 30, 169 (1993).

*Primary Examiner*—Johann Richter
*Assistant Examiner*—Laura R. C. Lutz
*Attorney, Agent, or Firm*—Teresa J. Welch; Stroud, Stroud, Willink, Thompson & Howard

[57] ABSTRACT

This invention relates to the use of heteroarenesulfonyl groups as protecting groups for amino groups, particularly the amino groups of amino acids, and specifically to nitrogen-protected (N-protected) amino acid reagents, which are particularly well-suited for use in peptide syntheses. In particular, the N-protected amino acid reagent is an N-heteroarenesulfonyl-protected amino acid halide. The heteroarenesulfonyl protecting groups are readily removed under relatively mild conditions.

8 Claims, 5 Drawing Sheets a: Zn/HOAc-EtOH
b: Al-Hg/ether-$H_2O$
c: 50% $H_3PO_2$
d: Zn/HCl-THF a: Zn/HOAc-EtOH
b: Al-Hg/ether-$H_2O$
c: 50% $H_3PO_2$
d: Zn/HCl-THF

N-HETEROARENESULFONYL-PROTECTED AMINO ACID REAGENTS FOR PEPTIDE SYNTHESIS

This invention was made with Government support under Grant No. R01 CA17918, ROI GM44724 and ROI CA38128 awarded by the National Institutes of Health and Grant No. CHE-9207513 awarded by the National Science Foundation. The U.S. Government has certain rights in this invention.

TECHNICAL FIELD

This invention relates generally to the use of heteroarenesulfonyl groups as protecting groups for amino groups, particularly the amino groups of amino acids, and specifically to nitrogen-protected (N-protected) amino acid reagents, which are particularly well-suited for use in peptide syntheses. In particular, the N-protected amino acid reagent is an N-heteroarenesulfonyl-protected amino acid halide.

BACKGROUND OF THE INVENTION

The rational synthesis of peptides has been a challenging task that has been solved only in the past few decades. The principal reaction in peptides synthesis is acylation of the amino group of one amino acid by the carboxyl group of another amino acid to form an amide bond. Since each amino acid has both an amino group and a carboxyl group, a direct approach leads to the formation of many different peptides. A general method that has been developed to avoid these difficulties involves the use of protecting (or blocking) groups, i.e., the use of certain groups to attach to the amino group or the carboxyl group of the amino acid and render the amino group or carboxyl group unreactive while still permitting the desired reaction to take place. Thus, the successful formation of the desired amide bond requires activation of the functional groups that participate in the bond forming reaction and protection of those that are not involved. Both amino and carboxyl protecting (or blocking) groups have been developed.

The carboxyl groups of amino acids are normally protected by conversion to an ester. Since esters are hydrolyzed more easily than amides, the protecting group can be removed readily by alkaline hydrolysis. Although simple methyl or ethyl esters have been used, benzyl and tert-butyl are most commonly employed because each of the latter can be removed under a variety of conditions. For example, the benzyl ester can be removed not only by alkaline hydrolysis but also by catalytic hydrogenation, $Li/NH_3$ reduction, or HBr/AcOH. The teft-butyl ester is significantly more stable to base and nucleophiles, but it can be readily cleaved under acidic conditions, such as with trifluoroacetic acid (TFA) alone or in organic solvents.

Protection of the amino group is a much more challenging task. Early efforts used the p-toluenesulfonyl (tosyl or Ts) group as the protecting group (E. Fischer, Chem. Ber., 48 (1915) 93). Sodium in liquid ammonia, for example, was used to cleave the Ts group (du Vigneaud et al., J. Am. Chem. Soc. 76 (1954), 3313). These methods are associated with a number of problems and find little use in modern peptide synthesis. Later efforts used alkoxycarbonyl protecting groups, e.g., the benzyloxycarbonyl (Cbz) and the t-butoxycarbonyl (Boc) groups. The Cbz group is readily introduced, and can be removed under a number of mild conditions, such as hydrogenolysis, $Na/NH_3$ reduction, etc. The Boc group is also readily introduced and can be cleaved with HCl in organic solvents, neat TFA or TFA in organic solvents. Still more recently, 9-fluorenylmethoxycarbonyl (Fmoc) group has found widespread applications in both solid-phase and solution peptide synthesis. The Fmoc group is remarkably stable to acidic conditions, but can be readily cleaved with secondary amines via a α-elimination mechanism. A problem with the use of the Fmoc group, however, is its high cost and large molecular weight which limits its use for large scale application.

To activate the N-acylamino acids for peptide coupling, they are converted to acid chlorides. A problem with acid chlorides derived from N-acylamino acids is that racemization is observed in the peptide coupling step because they undergo facile cyclization to the easily racemized oxazolinones. Although nitrogen protection using the alkoxycarbonyl protecting groups improves amino acid chloride stability in comparison to other acyl groups (e.g., formyl, acetyl, benzoyl), they can still cyclize to oxazolinones, especially if tertiary amines are present. Nonetheless, the Cbz, Boc and Fmoc groups remain the most popular amino protecting groups in peptide synthesis. Due to the success of alkoxycarbonyl protecting groups, sulfur- and phosphorus-based protecting groups have not been widely employed, although the use of arenesulfonamides as amine protective groups was recognized long ago (see, E. Fischer, supra). The known cleavage procedures suffer from harsh conditions and poor generality, and arenesulfonamide cleavage in the amino acid series has been difficult (see, e.g., Horner et al., Chem. Ber. 98 (1965) 3462; Kovas etal. J. Org. Chem. 31 (1996) 119; Rudinger et al., Helv. Chim. 56 (1973) 2216; Kestemont, Tetrahedron Lett. 32 (1991) 1425). Amino acid-derived benzenesulfonamides can be deprotected, but racemization occurs to the extent of 1.5–2.5% with typical amino acids (5% for phenylglycine). Kemp et al., Synthesis, 32 (1988), report the use of anthracene sulfonyl chloride as a protecting group for β-amino acids. The reported reaction involves the actual synthesis of the desired β-amino acid. Fukuyama et al., Tet. Lett. 36 (1995) 6373 report the use of p-nitrobenzenesulfonyl chloride as a protecting agent.

While the alkoxycarbonyl groups arguably possess very desired properties as an amine protecting group (i.e., ready introduction, crystallinity, stability under coupling conditions and multiple methods of removal), the racemization problem seems to be inherent in the alkoxylcarbonyl groups because the possibility of oxazolinone formation is always present. Oxazolinone derivatives are much more prone to racemization, especially in the presence of an amine base, which is often used as an additive. At the same time, sulfur-based protecting groups have met with limited success, and further, racemization can also occur. Despite recognition and study of various aspects of the problem, the prior art has produced very little in way of the introduction of a readily removable amine protective group in which removal can occur in relatively mild conditions and without racemization, i.e., an N-protected amino acid halide that does not participate in oxazolinone formation.

SUMMARY OF THE INVENTION

The present invention provides readily removable amine-protective groups in which removal of the protective group can occur in relatively mild conditions and without racemization. Specifically, the present invention relates to the use of heteroarenesulfonyl groups as amine or N-protective groups. These heteroarenesulfonyl groups bond with primary or secondary amines to protect the amino group from further reaction under conditions which permit modification of another portion of the molecule, e.g., formation of a peptide bond whereby an N-protected amino acid reacts with an unprotected amino portion of another amino acid. Removal or deprotection of these heteroarenesulfonyl groups of the present invention occurs in reaction conditions which are mildly acidic or neutral and are compatible with a variety of functional groups. The heteroarenesulfonyls of the present invention provide N-protected amino acid chlorides that have the reactivity of an acid chloride without the risk of oxazolinone formation, i.e., with minimal risk of racemization.

The foregoing, and other advantages of the present inventions, are realized in one aspect thereof in compounds which are represented by the formula (I)

$$G\text{-}SO_nZ \qquad \text{(I)}$$

wherein G is a heteroaryl group which is

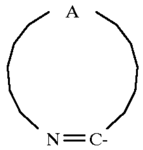

wherein A together with the N and C to which it is bonded form a 5 to 7-membered monocyclic heterocycle, a fused bicyclic heterocycle or a fused tricyclic heterocycle, any ring of which has carbon atoms and may have one to two additional heteroatoms (i.e., in addition to the N shown) selected from the group consisting of N, S and O; is a halogen which is Cl, F or Br, an amine residue, an amine acid residue or a peptide residue; and n is an integer from 0 to 2. Preferably, n is 2.

When compounds in accordance with the present invention are used to react with and protect an amino group, the compounds are amine- or nitrogen-protecting (N-protecting) reagents of formula (II)

$$G\text{—}SO_2X \qquad \text{(II)}$$

wherein G is a heteroaryl group as described hereinabove and X is Cl, F or Br. Preferably, X is Cl.

The preferred heteroarenesulfonyl group in accordance with the present invention is $$G\text{—}SO_2\text{—} \qquad \text{(III)}$$

Preferably, G is a group of formula (IV)

(IV)

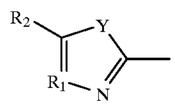

wherein Y is O, S or $NR_3$, where $R_3$ is H, a lower alkyl, aryl or aralkyl; $R_1$ is C, N, a lower alkyl, aryl or aralkyl; and $R_2$ is a saturated or unsaturated 1 to 4 atom chain, the atoms of which are selected from C, N or S. More preferred are compounds of formula (II) wherein Y is S or O, $R_1$ is N or C; and $R_2$ is methyl when $R_1$ is N, or alternatively when $R_1$ is C, $R_1$ and $R_2$, together with carbon to which they are bonded form an unsubstituted six-member aromatic hydrocarbon group; and X is Cl or F. More preferably, the heteroarenesulfonyl group of formula (III) is benzothiazole-2-sulfonyl (Bts), illustrated as formula (V) hereinafter, or 5-methyl-1,3,4-thiadiazole-2-sulfonyl (Ths), illustrated as formula (VI) fereinafter, and the compound of formula (II) is benzothiazole-2-sulfonyl chloride (BtsCl) or 5-methy-1,3,4-thiadiazole-2-sulfonyl chloride (ThsCl).

In an exemplary embodiment, the invention provides an amine-protected amino acid represented by the formula D-$H_n$N-(AA), wherein D is G—$SO_2$—and described in detail hereinafter. Preferably, the amino acid is N-protected with the thisyl (Ths) or betsyl (Bts) group, i.e., D is Ths or Bts. The amino acid is suitably an $\alpha$-amino acid, $\beta$-amino acid, or a $\gamma$-amino acid.

In a further aspect, the invention provides a method for amine-protecting or N-protecting an amino acid, comprising the step of reacting the amino acid with a reagent of formula (II) to yield an amine-protected amino acid. In an exemplary embodiment, a BtsCl or ThsCl reagent is reacted with an amino acid to yield a product which is a N-Bts- or N-Ths-amino acid, respectively.

In yet another aspect, the invention provides a method for peptide synthesis in which an N-heteroarenesulfonyl amino acid chloride is reacted with an amino ester under conditions sufficient to yield the desired dipeptide. The reaction is suitably carried out in a temperature range of 0° C. to room temperature and in the presence of $NaHCO_3/Na_2CO_3/H_2O/CH_2Cl_2$. The N-heteroarenesulfonyl amino acid chloride is preferably an N-Bts- or N-Ths-amino acid chloride. The resulting N-protected dipeptide is readily deprotected by reduction utilizing relatively mild reaction conditions, e.g., 50% $H_3PO_2$ at 50–60° C. or Zn/HOAc-EtOH, without measurable change in diastereomeric purity in the dipeptide.

The present invention is also suitable for providing a protected amine of formula D-$H_n$N-R, described hereinafter, and a method of deprotecting the amine. These constitute further aspects of the invention.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing wherein like designations refer to like elements throughout and in which.

DETAILED DESCRIPTION

Figure 1:
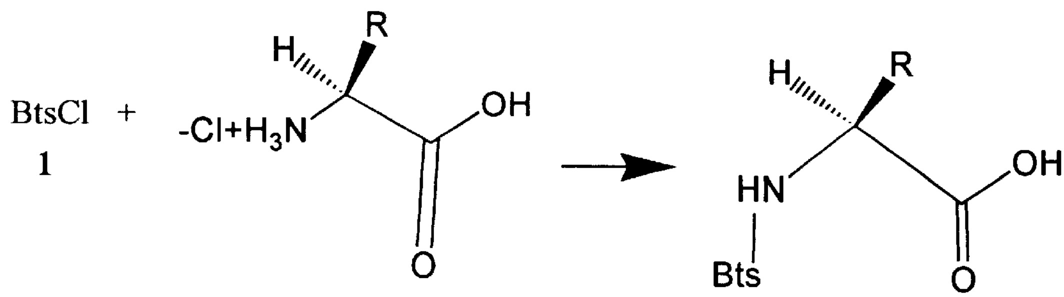
FIG. 1 illustrates an amine protection (N-protection) reaction for an amino acid in accordance with the present invention.
Figure 1:
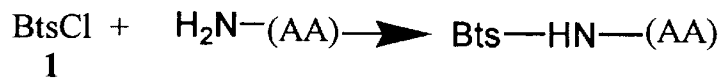
Figure 1:
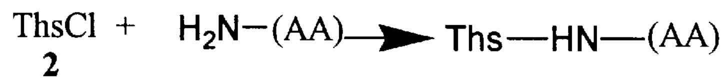

The present invention relates broadly to amine or nitrogen protective groups. However, the method of the present invention is particularly well-adapted for use in protecting of amino groups of amino acids and the subsequent use of the N-protected amino acids in peptide synthesis. Accordingly, the present invention will now be described in detail with respect to such endeavors; however, those skilled in the art will appreciate that such a description of the invention is meant to be exemplary only and should not be viewed as limitative on the full scope thereof.

The present invention provides heteroarenesulfonyl groups suitable for protection of an amino group, particularly an amino group of an amino acid. The present invention is characterized by an ability of the heteroarenesulfonyl groups to readily react with an amino group and to readily deprotect under mild reaction conditions without the risk of racemization.

In the following description of the method of the invention, process steps are carried out at room temperature (RT) and atmospheric pressure unless otherwise specified.

As used herein, the term "alkyl" refers to alkyl groups, typically containing one to six carbon atoms, which groups may be straight chain or branched. The term "aryl" refers to an aromatic ring containing six to ten ring carbon atoms. The term "aralkyl" refers to an aromatic ring substituted with an alkyl group. The term "heteroalkyl" or "heteroarene" refers to a hetero-aromatic ring such as a 5 to 7-membered monocyclic heterocycle, a fused bicyclic heterocycle or a fused tricyclic heterocycle, any ring of which has carbon atoms and one to three heteroatoms. Heterocyclic rings may contain nitrogen, sulfur or oxygen.

The terms "amine residue," "amino acid residue" and "peptide residue" are used herein. An "amine residue" is meant to refer to any alkyl or aryl moiety having an amino group minus an amino hydrogen. An "amino acid residue" is meant to refer to an amino acid or derivative thereof, such as an ester and the like, minus an amino hydrogen on the amino end of the molecule. A "peptide residue" is meant to refer to a peptide of two or more amino acids or derivatives thereof, such as an ester and the like, linked through an amide bond and having one less amino hydrogen on the amino end (i.e., the N-terminal) of the peptide.

Also used herein, the notation "(AA)" refers to an amino acid, generally. To refer to more than one amino acid, subscripts are used, e.g., $(AA)_1$, $(AA)_2$, etc. The notation "$H_2N$-(AA)" refers to an amine group of an amino acid, or if used in reference to a peptide, to the amine or N-terminal of the peptide. The notation "(AA)-OH" refers to a carboxyl group of an amino acid, or if used in reference to a peptide, to the carboxyl group or C-terminal of the peptide. As is conventional in the art, this notation can be used to denote specific amino acids. For example, to designate the amine group of alanine, the notation "$H_2N$-Ala" is used.

In reference to enantiomeric purity, "ee" is meant to refer to the enantiomeric excess value. The enantiomer excess ee is similar to optical purity; ee is the proportion of (major enantiomer) - (minor enantiomer). For example, a 90% optical purity is 90% ee, i.e., the enantiomer ratio is 95:5, major:minor. Similarly, "de" is the proportion of (major diastereomer) minus (minor diastereomer) in %.

It is also noted that, in addition to the standard chemical symbols, various abbreviations, well known in the art, are used herein for certain functional groups, e.g., "Me" for methyl, "Et" for ethyl, "i-Pr" for isopropyl, etc. It is further noted that, as is conventional in the art, parenthetical descriptions following, e.g., the name of a compound, may include various parameters such as reaction conditions, percent yields, etc.

In one aspect, the present invention provides heteroarenesulfonyl compounds of formula (I)

$$G—SO_nZ \qquad (I)$$

wherein G is a heteroaryl group which is

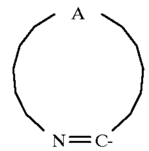

wherein A together with the N and C to which it is bonded form a 5 to 7-membered monocyclic heterocycle, a fused bicyclic heterocycle or a fused tricyclic heterocycle, any ring of which has carbon atoms and may have one to two additional heteroatoms (i.e., in addition to the N shown) selected from the group consisting of N, S and O; Z is a halogen which is Cl, F or Br, an amine residue, an amino acid residue or a peptide residue; and n is an integer from 0 to 2. Preferably n is 2.

In another aspect, the present invention provides an amine-protecting reagent, which is a heterosulfonyl halide of formula (II)

$$G—SO_2X \qquad (II)$$

wherein G is the heteroaryl group

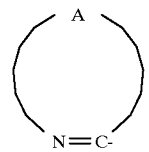

described hereinabove and X is Cl, F or Br. That is, when compounds in accordance with the present invention are used to react with and protect an amino group, the compounds are amine- or nitrogen-protecting (N-protecting) reagents of formula (II). Thus, the preferred heteroarenesulfonyl group in accordance with the present invention is given by formula (III)

$$G—SO_2X \qquad (III)$$

and wherein Z is X which is a halide, preferably Cl.

Preferably, G is a group of formula (IV)

(IV)

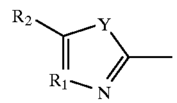

wherein Y is O, S or $NR_3$, where $R_3$ is H, a lower alkyl, aryl or aralkyl; $R_1$ is C, N, a lower alkyl, aryl or aralkyl; and $R_2$ is a saturated or unsaturated 1 to 4 atom chain, the atoms of which are selected from C, N or S. More preferred are groups of formula (III) wherein Y is S or O, $R_1$ is N or C; and $R_2$ is methyl when $R_1$ is N, or alternatively when $R_1$ is C, $R_1$ and $R_2$, together with carbon to which they are bonded form an unsubstituted six-member aromatic hydrocarbon group; and X is Cl or F. Most preferred is the benzothiazole-2-sulfonyl (Bts) group represented by formula (V)

(V)

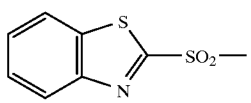

and the 5-methyl-1,3,4-thiadiazole sulfonyl (Ths), represented by formula (VI)

(VI)

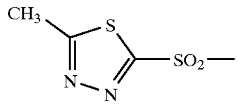

More preferred are the reagents of formula (II) which are benzothiazole-2-sulfonyl chloride (BtsCl, also referred to herein as reference numeral (1)) or 5-methy-1,3,4-thiadiazole-2-sulfonyl chloride (ThsCl, also referred to herein as reference numeral (2)).

The reagents of formula (II) are readily synthesized utilizing appropriate modifications of the methods of Roblin et al., J. Am. Chem. Soc. 72 (1950) 4890 and Stanovnik et al., Arch. Pharm. 298 (1965) 357, both of which are incorporated herein by reference. The preferred heteroarenesulfonyl chlorides of the present invention, BtsCl (1) and ThsCl (2), are prepared from commercially available 2-mercaptobenzothiazole and 2-mercapto-5-methyl-1,3,4-thiadiazole, respectively. Each of these starting materials is treated with chlorine in acetic acid-water (HOAc-$H_2O$). The resulting crystalline (1) or (2) is stable for months in the freezer, but evolution of $SO_2$ is apparent after several days or less at room temperature (RT), depending on crystal quality.

The heteroarenesulfonyl reagents of formula (II) are advantageously utilized to protect nitrogen or amino groups. The reagents of formula (II) readily react with amines or amino acids to yield N-protected amines or N-protected amino acids. A protection reaction in accordance with the present invention is illustrated in FIG. 1 wherein "R" is a general organic moiety and exemplifying the BtsCl reagent. This protection reaction occurs in aqueous suspension or modified nonaqueous conditions. The amino acids which are protectible in accordance with the present invention suitably include α-amino acids such as those normally found in naturally as well as unnaturally occurring peptides (illustrated in FIG. 1), β-amino acids such a β-alanine and γ-amino acids such a γ-aminobutyric acid. As used herein, the N-protected amino acids in accordance with the present invention are referred to by the shorthand structural notation "D-$H_n$N-(AA)" where D is a heteroarenesulfonyl group, G—$SO_n$—, in accordance with the present invention, e.g., Bts or Ths, (AA) represents any amino acid and n is an integer which is zero or 1, or in conventional nomenclature expression, may be written simply as N-D-(AA), e.g., N-Ths-Ala.

To yield N-protected amines, simple amines react rapidly with BtsCl (1) and ThsCl (2) under aprotic conditions. With zwitterionic amino acids, best results are achieved by stirring a suspension of BtsCl (1) or ThsCl (2) in a solution of the amino acid in sodium hydroxide-water (NaOH-$H_2O$) while maintaining pH in the range 10–10.5 to maximize the rate of N-sulfonylation compared to the rate of BtsCl or ThsCl hydrolysis. This method afforded crystalline N-Bts and N-Ths derivatives in 92–97% yield with alanine, valine, phenylalanine, proline, and phenylglycine (Phg). The N-Ths derivatives formed significantly faster (2 hours (h) at 0° C. for N-Ths-phenylglycine (N-Ths-Phg) vs. 10 h at 10° C. for N-Bts-Phg), probably because ThsCl has greater water solubility compared to BtsCl. Under similar conditions, but using 3.1 equivalents (equiv) of ThsCl, both amino groups of lysine were protected ($N_\alpha$,$N_\epsilon$-bis-Ths-Lys, 89%). Serine reacted selectively at the amino group using 1.5 equiv ThsCl (74% N-Ths-Ser isolated), but similar treatment with BtsCl afforded a mixture of products. The standard method produced the mono-Bts derivative of tryptophan (>95% yield) without affecting the indole nitrogen.

Tyrosine gave the bis-sulfonylation product using 3.1 equiv of ThsCl at pH 10 (90%), but O-sulfonylation could be prevented by temporary O-silylation. Thus, heating with bistrimethylsilylacetamide (2.1 mol equiv, $CH_3CN$), followed by reaction with BtsCl in pyridine and an aqueous workup afforded N-Bts-Tyr in 72% yield. Modified nonaqueous conditions were also used to prepare N-Bts-Phg from Phg +$Me_3SiCl/Et_3N$ (THF, reflux), followed by BtsCl/$Et_3N$ and workup with 0.5 M HCl to give N-Bts-Phg in 87% yield.

Figure 2:
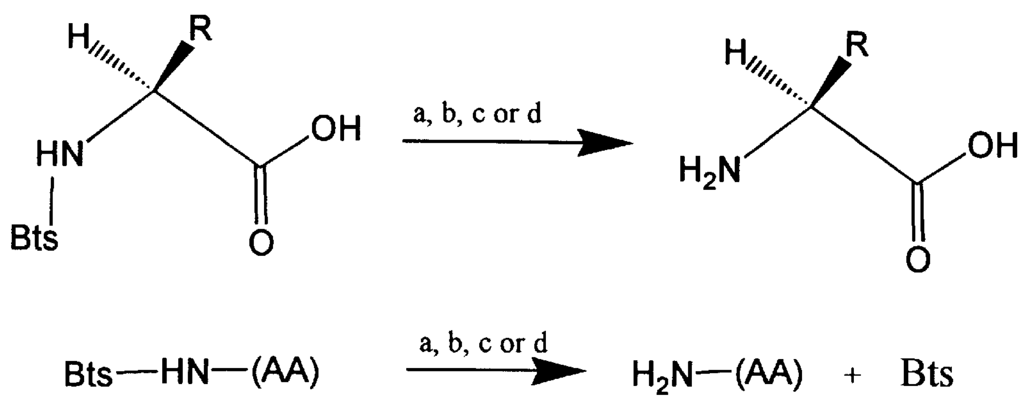
FIG. 2 illustrates a deprotection reaction for a N-heteroarenesulfonyl protected amino acid.

Removal or deprotection of the heteroarenesulfonyl groups in accordance with the present invention is advantageously accomplished in relatively mild conditions. The general reaction scheme is illustrated in FIG. 2, exemplifying the protected amino acid of FIG. 1. Specifically, deprotection of the N-Bts or N-Ths group is accomplished at room temperature by treatment with zinc in ethanolic acetic acid (Zn/HOAc-EtOH) or aluminum amalgam in ether-water (Al-Hg/ether-H2O), or at higher temperatures using excess 50% hypophosphorous acid ($H_3PO2$) (slow addition; tetrahydrofuran-water (THF-$H_2O$), reflux), and sodium dithionite ($Na_2S_2O_4$) or sodium hydrogen sulfite ($NaHSO_3$) (EtOH-$H_2O$, reflux). The most convenient deprotection conditions, i.e.,Zn, Al-Hg, or $H_3PO_2$, do not cleave p-toluenesulfonamides in control experiments, indicating that the electron-withdrawing heterocycle activates the sulfone for reduction.

Figure 6A:
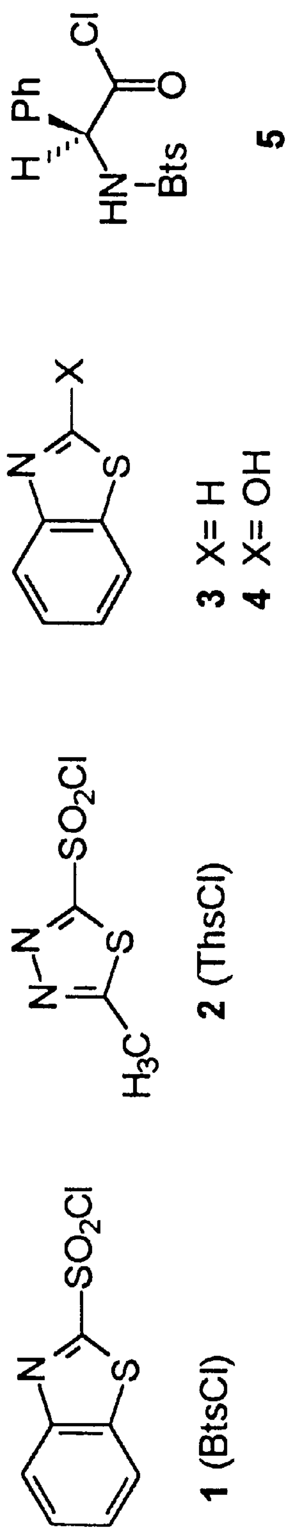
FIG. 6A and 6B illustrates molecular structures and specific dipeptide synthesis reactions tested in accordance with the present invention.
Figure 6A:
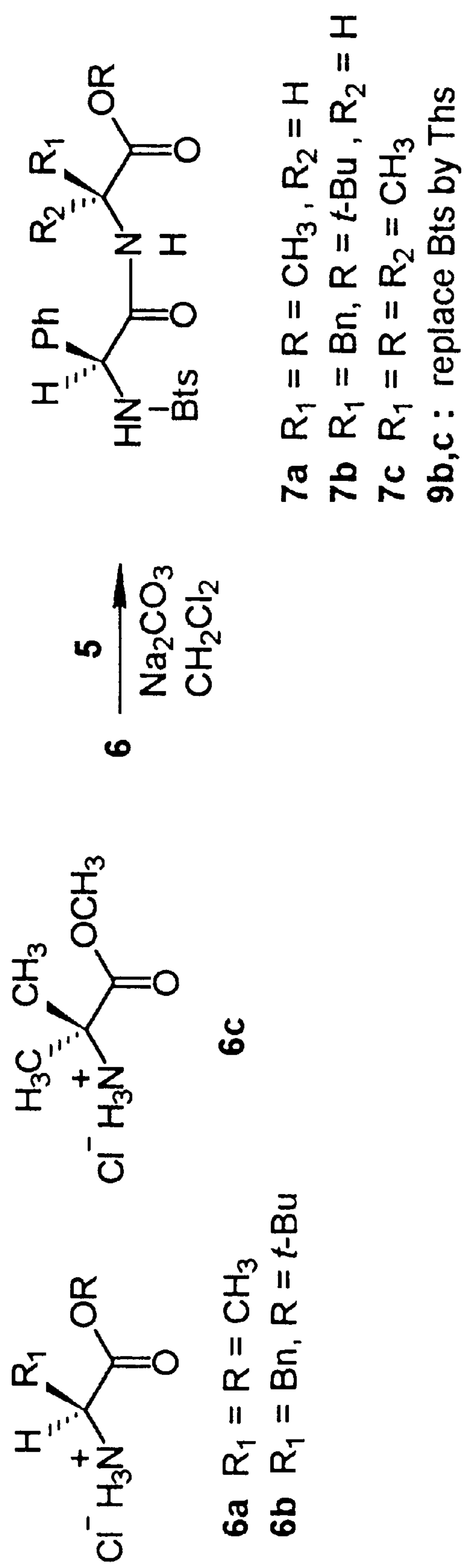
Figure 6B:
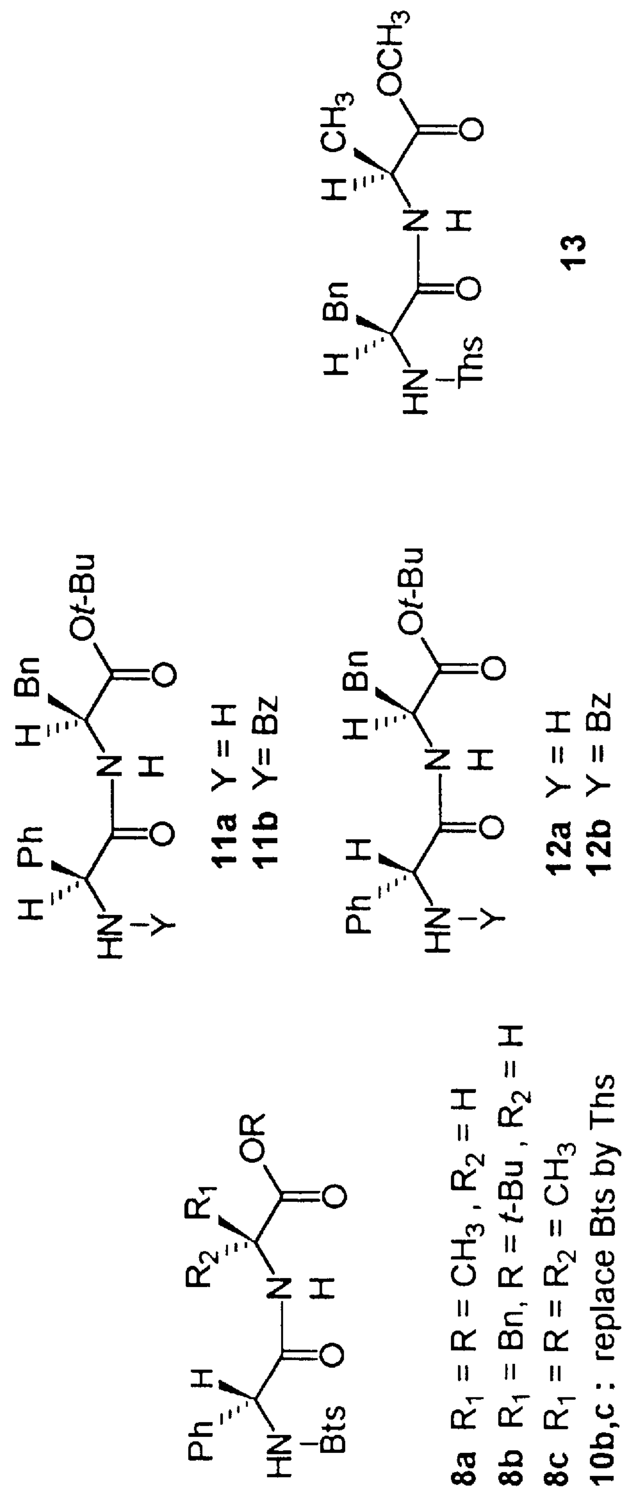

Deprotection of N-Bts-Phg with Zn/HOAc-EtOH at room temperature (14 h) produced Phg, quantitative yield, 99.9% ee by chiral stationary phase-high pressure liquid chromatography (CSP-HPLC) assay after conversion to the 3,5-dinitrobenzamide (DNB). Deprotection by the dropwise addition of excess 50% aqueous $H_3PO_2$ at 50° C over 2 hours (h) gave Phg with 99.5% ee (93% yield). Benzothiazole (3) (structure shown in FIG. 6 A and 6B) was formed as the byproduct of reductive cleavage and was easily separated by organic extraction. Deprotection of N-Ths-Phg yielded>99.8% ee using Zn/HOAc-EtOH, Zn/HCl-THF, Al-Hg/THF-$H_2O$ (>90% yield). Strong acid treatment cleaved N-Ths-Phg (2M HCl/MeOH, 30 h RT reflux; 99.6% ee), but no reaction was detected in $CF_3CO_2H$ solution at room temperature (2 days). Slow cleavage did occur in $CF_3CO_2H/C_6H_5SH$ (ca. 25%, 2 days RT). Deprotection with sodium hydroxide (NaOH) was effective for N-Bts-Pro (2.5 M NaOH: RT, 12 h,>99.8% ee by CSP-HPLC after conversion to DNB-Pro-OMe; neutral byproduct: 2-hydroxybenzothiazole (4) as shown in FIG. 6A and 6B), but harsher conditions were needed for N-Bts-Phg (1 M NaOH, 90–100° C., 24 h; 14% ee), probably because deprotonation of the Bts-NH subunit retards attack by hydroxide.

Figure 3:
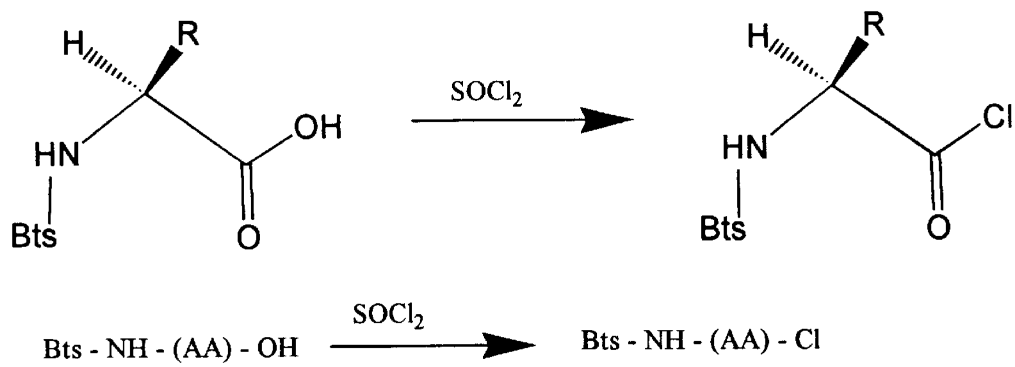
FIG. 3 illustrates the formation of an N-protected amino acid chloride from an N-protected amino acid in accordance with the present invention.

The N-protected amino acids are suitably reacted with thionyl chloride to yield N-protected amino acid chlorides. The general reaction scheme is illustrated in FIG. 3, again exemplifying the Bts group.

Figure 4:
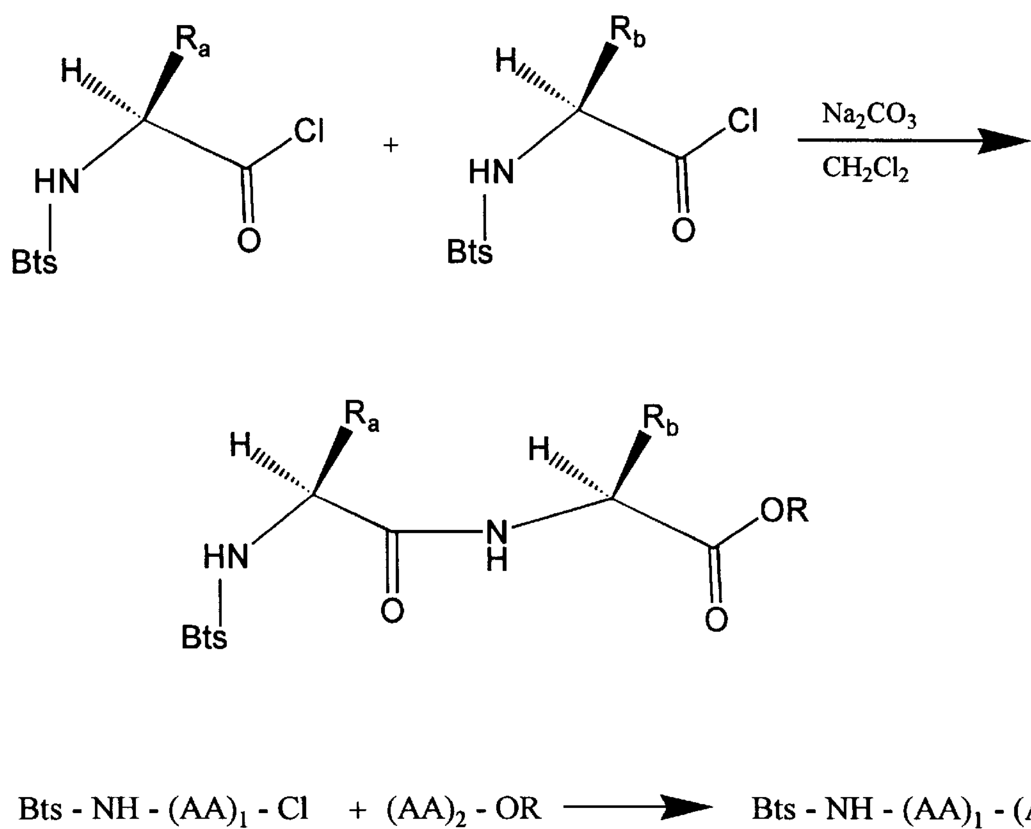
FIG. 4 illustrates a dipeptide formation reaction in which one of the amino acids is N-protected with the betsyl group.
Figure 5:
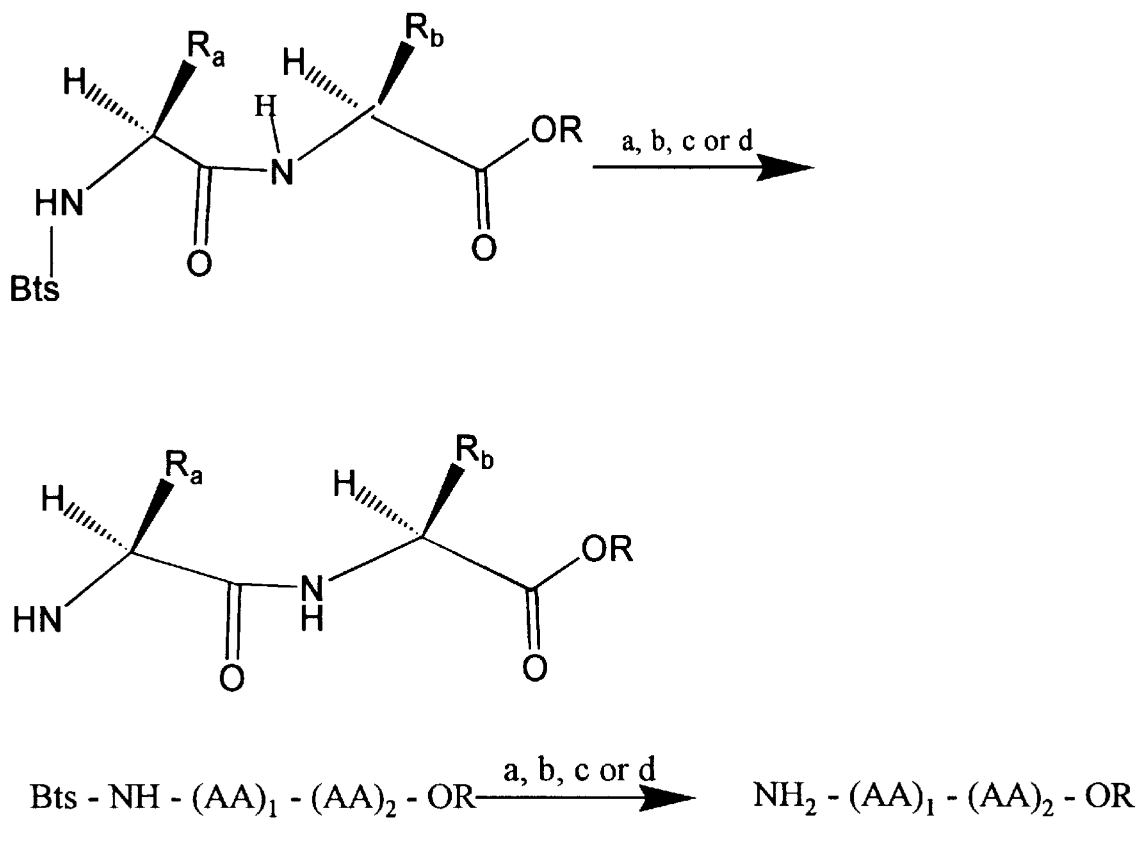
FIG. 5 illustrates a deprotection reaction for the N-Bts-protected dipeptide of FIG. 4.

N-protected amino acid chlorides are advantageously used to effect peptide synthesis, the coupling with representative amino acid esters occurring rapidly under two phase aqueous conditions with minimal racemization in the coupling step. The general coupling reaction scheme is illustrated in FIG. 4 and the deprotection reaction scheme is illustrated in FIG. 5. In both FIGS. 4 and 5, the Bts group is exemplified and "$R_a$" and "$R_b$" are general organic moieties of each of the amino acid residues, which moieties may be the same or different. As used herein, an N-protected dipeptide is represented by the general shorthand structural formula of "D-$H_n$N-$(AA)_1$-$(AA)_2$-OR", where D is a heteroarenesulfonyl group in accordance with the present invention, which is preferably the betsyl or thisyl group, $H_n$N represents the protected amino group of $(AA)_1$; $(AA)_1$ and $(AA)_2$ are the same or different amino acids and OR represents the ester group of $(AA)_2$. The integer n is 0 or 1. Also, as used herein, the written name of such dipeptide is given as N-D-$(AA)_1$-$(AA)_2$-OR, e.g., N-Ths-Ala-Gly-OR.

For the formation of a simple dipeptide, as shown in FIGS. 4 and 5, an N-protected amino acid chloride in accordance with the present invention is reacted with a carboxyl protected amino acid, e.g., an amino ester, to form an N-protected dipeptide. The dipeptide is then deprotected. These steps can be repeated, i.e., the dipeptide reacted with another N-protected amino acid chloride in accordance with the present invention to form a tripeptide. The coupling and deprotection can be repeated until a peptide of preselected length and sequence is formed. The coupling and deprotection reactions are all carried out while essentially maintaining enantiomeric and diastereomeric purity.

Reference is now made to FIG. 6A and 6B. The sensitive Phg system was used to form a dipeptide and to test % retention of configuration, i.e., to examine retention of enantiomeric purity (structures and reactions for which are illustrated in FIG. 6A and 6B). Recrystallized N-Bts-(S)-Phg was heated with 3 equiv $SOCl_2$ in $CH_2Cl_2$, volatiles were removed under vacuum, and the crude acid chloride (5) was reacted with amino esters (6) (two-phase conditions, $H_2O$/$Na_2CO_3$-$NaHCO_3$/$CH_2Cl_2$, 0–5° C., 1 5 min). Protected dipeptides (7) were isolated in high yield by crystallization from the crude product (7*a*: 95%, 7*b*: 89%, 7*c:* 95% crude solid, 87% recrystallized), indicating essentially complete coupling despite the short reaction time.

To fully evaluate the activation-coupling technique, the Phg configuration in (7) was assayed prior to crystallization. The minor diastereomers (8*a*, 8*b*) and the enantiomer (8*c*) were prepared independently to establish detection limits in the crude products (7*a*, $CH_3O^{13}C$ satellite vs. 8*a* $^1H$ $CH_3O$ signal, <0.1% 8*a* detectable; 7*b*, t-BuO $^{13}C$ satellite vs. $^1H$ t-BuO signal, 0.1% detectable; 7*c*, <0.1% (8*c*) detectable, CSP-HPLC), as well as assay error (7*a*/8*a*, ±0.1%; 7*b*/8*b*, ±0.2% crude, ±0.1% after crystallization; 7*c*/8*c*,±0.05%). No equally sensitive assay for N-Bts-Phg was found, so the overall results were evaluated by comparing ee of the commercial starting materials (CSP-HPLC: S-Phg, >99.9% ee; R-Phg, 99.2% ee; 6*a*, 99.6% ee; 6*b* ≧99.8% ee) with the de of 7*a,b*/8*a,b* or the ee of 7*c*/8*c*.

Diastereomer purity in crude (7*a*) (99.7% de) and (7*b*) (99.6% de) and enantiomeric purity in crude (7*c*) (99.8 % ee) was consistent with a maximum of 0.1% racemization of the Phg subunit (>99.8% retention) after allowing for experimental error and the purity of commercial reagents. The assay includes potential racemization in the $SOCl_2$ activation and the two-phase coupling steps. In earlier studies, Carpino et al., J. Org. Chem. 56 (1991) 2611, have shown that the N-protected acyl fluoride (Cbz-Phg-F) reacts with the methyl ester of α-amino isobutyric acid (Aib-$OCH_3$) or with proline amide to give the dipeptides Cbz-Phg-Aib-$OCH_3$ (<1% racemization) and Cbz-Phg-Pro$NH_2$ (<0.1% diastereomer formation). The results with N-Bts-Phg-Cl were advantageous in view of the simple reagents, methods, and short reaction time for coupling.

Crystallization of the protected dipeptide (7*b*) removed trace impurities and improved $^{13}C$ satellite assay precision (99.8% de). Purified (7*b*) was deprotected by the slow addition of 50% $H_3PO_2$, and refluxing with THF-$H_2O$); the resulting (11*a*) was converted into the more stable (11*b*) (BzCl/NEt(i-Pr)$_2$/$CH_2Cl_2$; 99% yield overall, 99.8% de; <0.1% diastereomer detection limit, $^{13}C$ satellite method). High yields (>90%) were also obtained using other reducing agents for deprotection, but significant epimerization was detected in (11*b*) (24 mol equiv $Na_2S_2O_4$/EtOH-$H_2O$ reflux, 2 h, 97% de; 43 mol equiv $NaHSO_3$, EtOH-$H_2O$, 6 h reflux, 88% de) in contrast to the $H_3PO_2$ results.

Similar reactions were undertaken in the N-Ths-Phg series without optimizing yields for individual examples. Thus, warming recrystallized N-Ths-(S)-Phg or N-Ths-(R)-Phg with thionyl chloride followed by reaction with (6*c*) using 2-phase conditions (aqueous $Na_2CO_3$/$CH_2Cl_2$) produced (9*c*) or (10*c*) (64%). The enantiomers were distinguished by the chemical shift of the ths C-$CH_3$ signal in the presence of a chiral europium shift reagent (≅99.8% ee, $^{13}C$ satellite method; detection limit based on an authentic 99.7:0.3 mixture). Similarly, the N-Ths-Phg-Phe-OC$(CH_3)_3$ diastereomers (9*b*) and (10*b*) were obtained starting from (6*b*) and (S)-Ths-Phg and (R)-Ths-Phg, respectively (86–7% yield, ≧99.8% de). Deprotection of (9*b*) with Zn-HOAc followed by N-benzoylation afforded (11*b*) (92% overall, 99.8% de) and similar treatment of (10*b*) produced (12*b*) (≧99.7% de). Reaction of (9*b*) with $Na_2S_2O_4$/EtOH-$H_2O$ (reflux) followed by benzoylation gave significant epimerization in (11*b*) (96% de), as also found in Bts cleavge from (7*b*) using this reagent. However, the standard $H_3PO_2$ deprotection of (9*b*) produced (11*b*) with 99.8% de (95% overall yield). Thus, the Bts and Ths protecting groups have very similar chemical properties in the context of the peptide coupling applications. The Bts group is advantageous in terms of cost because the starting material for synthesis, 2-mercaptobenzothiazole, is cheaper. On the other hand, the Ths group has advantages in the rate of N-protection (aqueous suspension method), solubility, and crystallinity in some cases.

Another dipeptide example involved treating (S)-phenylalanine (99.6% ee) with ThsCl followed by thionyl chloride as usual. The resulting crude N-Ths-(S)-Phe-Cl was reacted with (6*a*) (99.6% ee) to give (13) in 70–75% overall yield ($Na_2CO_3$-$H_2O$/$CH_2Cl_2$ conditions). The thisyl C-$CH_3$ $^1H$ NMR signals of the diastereomers were resolved and 99.6% de was determined ($^{13}C$ satellite method). However, if the crude N-Ths-(S)-Phe-Cl was recrystallized, then coupling with (6*a*) as before gave (13) with >99.8% de.

In summary, the Bts and Ths groups allow conversion of phenylglycine to the protected acid chloride (5). Rapid coupling occurs with (6*a,b,c*) in the absence of additives, and the demanding Aib-OMe substrate affords (7*c*) with 99.8% ee. Deprotection of diastereomers (7*b*/8*b*) and (9*b*/10*b*) is possible without change in de using the inexpensive Zn/HOAc-EtOH or 50% $H_3PO_2$. The latter procedure involves homogeneous (moderately acidic) reducing conditions. No reported prior use of $H_3PO_2$ in peptide synthesis or in N-deprotection has been found. Other Bts- or Ths-protected amines, lacking a $CO_2H$ group, can also be easily made and deprotected. However, there are few alternatives that allow preparation of stable amino acid chlorides. The Bts-protected amino acid chlorides are practical reagents for difficult solution phase peptide coupling reactions or for other applications where the high reactivity of an acid chloride is important.

The present invention is further explained by the following examples which should not be construed by way of limiting the scope of the present invention.

EXAMPLE 1

Preparation of Benzothiazole-2-sulfonyl Chloride (BtsCl) (1)

BtsCl (1) was prepared in accordance with the methods of Roblin et al., J. Am. Chem. Soc. 72 (1950) 4890, and Stanovnik et al., Arch. Pharm. 298 (1965) 357, both of which are incorporated herein by reference. To 60 mL of magnetically stirred 33% aq acetic acid cooled to 0° C. (ice-salt bath), $Cl_2$ gas was introduced. After a yellow precipitate formed, a dispersion of 2-mercaptobenzothiazole (Aldrich, 10.0 g, 60 mmol) in 60 mL of 33% aqueous (aq) acetic acid was added in ca. 20 portions over 2 h while the internal reaction temperature was maintained at 0 to 50° C. (2-mercaptobenzothiazole can also be added as a solid instead of the suspension in aq acetic acid; however, the addition of the solid is complicated by reaction with $Cl_2$ gas that makes the solid stick to the spatula). The rate of $Cl_2$ bubbling was controlled so that fluffy crystals of $Cl_2$ clathrate could be seen in the suspension (large excess of chlorine at all times is critical for a successful reaction; otherwise, the disulfide byproduct may precipitate, resulting in side products apparently derived from ring chlorination of the disulfide).

The yellow suspension was stirred at 0° C. for an additional 15 min. The mixture was then suction filtered with an ice-cooled funnel, the solid was washed with 100 mL of ice water, dissolved in 100 mL of cold $CH_2Cl_2$, and the clear solution was washed successively with 100 mL of cold saturated $NaHCO_3$ solution and 100 mL of cold brine. The organic phase was dried (4 A° molecular sieves, activated powder) at −20 to 0° C. for 1 h, and then filtered through celite. The beige solution was concentrated under diminished pressure at 10° C. and dry ether (20 mL) was added to the thick slurry. The suspension was cooled in a dry ice-acetone bath, filtered by suction, and the solid washed with 10 mL of cooled dry ether. The crystals were dried under vacuum for 10 min to give benzothiazole-2-sulfonyl chloride (BtsCl) (1) as off-white needles [(9.6–10.0 g, 69–72%); mp 105–108° C. dec (lit. mp 108–110° C.; 101–105° C.) $^1H$ NMR ($CDCl_3$)δ6 8.35–8.26 (m, 1H) 8.10–8.01 (m, 1H) 7.76–7.66 (m, 2H)].

The product can be stored in the freezer for several months. Freshly prepared BtsCl is stable at RT for several hours, but decomposition is noticeable after several days by the smell of $SO_2$.

If desired, $Na_2SO_4$ could be used instead of molecular sieves to dry the dichloromethane extract. In this case, the final product contained up to 15 mol% of $H_2O$; however, the moist material was satisfactory for the protection of amino acids under the usual conditions.

EXAMPLE 2

Preparation of 5-Methyl-1,3,4-thiadiazole-2-sulfonyl Chloride (ThsCl) (2)

ThsCl (2) was prepared using the procedure described for BtsCl in Example 1 except that solid 5-methyl-1 3,4-thiadiazole-2-thiol instead of a suspension in aq acetic acid was added over 30 min; ether was used instead of $CH_2Cl_2$ for extraction; and $Na_2SO_4$ was employed to dry the organic phase instead of molecular sieves. The ThsCl (2) was obtained in 80% yield as a white solid [mp 44–48° C. dec after recrystallization from ether; 200 MHz NMR ($CDCl_3$, ppm)δ2.98 (3H, s). Analytical TLC on silica gel, EtOAc, $R_f$=0.60; molecular ion calcd for $C_3H_3ClN_2O_2S_2$: 197.93257; found m/e=197.9304, error=10 ppm].

The moist material thus obtained was used for amino acid protection as described hereinbelow. If desired, the material can be dried under vacuum over $P_2O_5$ for 2 h to give ThsCl (2) containing <5% water according to the NMR integral.

The decomposition of ThsCl is noticeable upon storage for a few hours at RT by the smell of $SO_2$, but the crystalline product can be stored for months in the freezer. The purified N-Ths derivatives are stable and can be stored indefinitely in the refrigerator.

Preparation of N-Protected Amino Acids

EXAMPLE 3

Preparation of N-Bts-(R)-phenylglycine and N-Bts (S)-phenylglycine (R)-Phenylglycine (Aldrich, 0.483 g, 3.20 mmol) was dissolved in 0.25 M aq NaOH (11 mL, 2.8 mmol) at 10° C. Solid betsyl chloride (1) (1.10 g, 4.72 mmol) was added in one portion and the suspension was stirred for 10 h at 10° C. The reaction was monitored throughout using a pH meter and was maintained at pH=10–10.5 by addition of 1.3 M NaOH (total 5 mL, 6.5 mmol). Initially, it was necessary to adjust pH every 15–30 min, but during the second half of the reaction, monitoring was needed at 30–60 min intervals. It was found that at higher pH, hydrolysis of the BtsCl became fast and lower yields resulted.

The cloudy solution was extracted with ether (10 mL) to remove organic soluble material, the aqueous phase was acidified to pH 1 with concentrated HCl, and was then extracted with 3×10 mL of EtOAc. The combined EtOAc extracts were dried ($Na_2SO_4$) and concentrated, affording the product (5) as white, fine crystals [1.09 g, 97%, >98% pure by NMR assay; analytical TLC on silica gel, 20:10:1 EtOAc/hexane/HOAc, $R_f$=0.38]. Pure material (5) was obtained by crystallization from ethyl acetate/chloroform [mp 165.5–162° C. dec; $[\alpha]_D^{25}$−138 (c=2.0, EtOH); molecular ion calcd for $C_{15}H_{13}N_2O_4S_2$(M+H): 349.0317; high resolution fast atom bombardment mass spectroscopy (HRFAB) found m/e=349.0319, error=1 ppm; IR ($CHCl_3$, $cm^{-1}$) 3348, N-H; 1703, C=O; 300 MHz NMR ($CD_3CN$, ppm)δ8.1–8.0 (2H, m) 7.7–7.5 (2H, m) 7.4–7.2 (6H, m) 5.37 (1H, d, J=7.5 Hz)].

The S-enantiomer was prepared in the same way from S-phenylglycine, $[\alpha]_D^{25}$+139 (c=2.0, EtOH).

EXAMPLE 4

Preparation of N-Ths-(S)-Phenylglycine

A similar procedure to the above was used to prepare N-Ths-(S)-Phg, but the reaction was performed at 0° C. and was complete after two hours of stirring. The reaction was considerably faster than in the BtsCl case, probably because ThsCl is more soluble than BtsCl. It was necessary to monitor pH throughout the initial stages and to add the NaOH solution dropwise at typical titration speed to control pH. Yield, 92% after crystallization from warm EtOAc/hexane [mp 176–178° C., fine white crystals; analytical TLC on silica gel, 20:1 EtOAc/AcOH, $R_f$=0.31; HRFAB found for $C_{11}H_{12}N_3O_4S_2$(M+H):

314.0265, error=2 ppm; IR (KBr, $cm^{-1}$) 3299, N-H; 1712, C=O; 1733, C=O; 300 MHz NMR ($CD_3CN$, ppm)δ9.9–9.2 (1 H, br) 7.4–7.2 (6H, m) 5.30 (IH, d, J=8.7 Hz) 2.74 (3H, s)].

The general procedures of Examples 3 and 4 were used to prepare the following compounds of Examples 5–17; the preparation of Bts derivatives was performed at 10° C. (10 h), and the Ths derivatives were made at 0° C. (2 h). Any modifications to the general procedures are detailed in the specific examples.

EXAMPLE 5

Preparation of N-Bts-(S)-phenylalanine

Yield, 97%; analytical TLC on silica gel, 20/10/1 EtOAc/hexane/HOAc, $R_f$=0.51. Pure material was obtained by crystallization from EtOAc/chloroform [mp 151–152° C. dec; $[\alpha]_D^{25}$ −6.6 (c=2.1, ETOH); molecular ion calcd for $C_{16}$, $H_{15}N_2O_4S_2$ (M+H): 363.0473; HRFAB found m/e=363.0470, error=1 ppm; IR ($CHCl_3$, $cm^{-1}$) 3333, N-H; 1734, C=O; 300 MHz NMR ($CD_3CN$, ppm)δ8.1–8.0 (2H, m) 7.7–7.5 (2H, m) 7.2–7.0 (5H, m) 6.75 (1H, d, J=9.0 Hz) 4.47 (1H, ddd, J=9.1, 9.0, 4.9 Hz) 3.17 (1H, dd, J=13.9, 4.9 Hz) 2.89 (1H, dd, J=13.91 9.1 Hz)].

EXAMPLE 6

Preparation of N-Ths-(S)-phenylalanine

Yield, 96%, crystallization from hot EtOAc/hexane [mp 179.5–180.0° C., colorless blocks; analytical TLC on silica gel, 20:1 EtOAc/AcOH, $R_f$=0.27; HRFAB found for $C_{12}H_{14}N_3O_4S_2$(M+H): 328.0415, error=4 ppm; IR (KBr, $cm^{-1}$) 3284, N-H; 1697, C=O; 1366, S=O; 300 MHz NMR ($CD_3CN$, ppm)δ6 9.6–8.5 (1H, br) 7.3–7.1 (5H, m) 6.79 (1H, br, d, J=8.9 Hz) 4.38 (1H, ddd, J=9.0, 8.9, 4.9 Hz) 3.17 (1H, dd, J=13.9, 4.9 Hz) 2.89 (1H, dd, J=13.9, 9.0 Hz) 2.74 (3H, s)].

EXAMPLE 7

Preparation of N-Bts-(S)-valine

Yield, 94%, analytical TLC on silica gel,20:10:1, EtOAc/hexane/HOAc, $R_f$=0.68. Pure material was obtained by crystallization from chloroform [mp 101–103° C.; $[\alpha]_D^{25}$+29.8 (c=2.3, EtOH); molecular ion calcd for $C_{12}H_{,15}N_2O_4S_2$ (M+H): 315.0473; HRFAB found m/e=315.0479, error=2 ppm; IR ($CHCl_3$, $cm^{-1}$) 3333, N-H; 1722, C=O; 300 MHz NMR ($CD_3CN$, ppm) δ8.1–8.0 (2H, m) 7.7–7.5 (2H, m) 6.65 (1H, br, d, J=9.1 Hz) 4.11 (1H, dd, J=9.1, 4.9 Hz) 2.2–2.1 (1H, m) 1.92 (3H, d, J=6.8 Hz) 0.84 (3H, d, J=6.8 Hz)]. Example 8: Preparation of N-Ths-glycine Yield, 82%, crystallization from $CH_3CN/CHCl_3$; analytical tlc on silica gel, 20:1 EtOAc/AcOH, $R_f$=0.25 [mp 159.0–159.5° C., colorless blocks. HRFAB found for $C_5H_8N_3O_4S_2$ (M+H): 237.9964, error=3 ppm; IR (KBr, $cm^{-1}$) 3260, N-H; 1718, C=O; 1450, S=O; 200 MHz NMR ($CD_3CN$, ppm) δ8.0–9.5 (1H, br) 6.9–6.4 (1H, br) 3.97 (2H, s) 2.79 (3H, s)].

EXAMPLE 9

Preparation of N-Bts-(S)-alanine

Yield, 99% by crystallization from hot chloroform/hexane; analytical TLC on silica gel, 1:20 AcOH/EtOAc, $R_f$=0.56. Pure material was obtained by crystallization from EtOAc/hexane [mp 140–141 ° C., dec; $[\alpha]_D^{25}$−2.5 (c=3.5, EtOH; molecular ion calcd for $C_{10}H_{10}N_2O_4S_2$: 286.00824; found m/e =286.0079, error=1 ppm; IR (KBr, $cm^{-1}$) 3226, N-H; 1726, C=O; 300 MHz NMR ($CD_3CN$, ppm)δ9.25 (1 H, br, s) 8.11–8.03 (1H, m) 7.99–7.91 (1H, m) 7.60–7.51 (2H, m) 6.36 (1H, br, d, J=7.9 Hz) 4.41 (1H, pent, J=7.3 Hz) 1.51 (3H, d, J=7.3 Hz)].

EXAMPLE 10

Preparation of N-Ths-(S)-alanine

The preparation entailed a modified isolation due to water solubility. The acidified reaction mixture was evaporated (aspirator); the solid residue was extracted with EtOAc, filtered, and the product was precipitated using hot hexane to yield 94% of the product, >98% pure by NMR assay; analytical TLC on silica gel, 1:20 AcOH/EtOAc, $R_f$=0.26. Pure material was obtained by crystallization from EtOAc/hexane [mp 136.0–136.5° C.; $[\alpha]_D^{25}$ +9.9 (c=2.1, EtOH); molecular ion calcd for $C_6H_{10}N_3O_4S_2$(M+H): 252.01134, found m/e=252.011 1, error=1 ppm; IR (KBr, $cm^{-1}$) 3222, N-H; 1738, C=O; 300 MHz NMR ($CD_3CN$, ppm) δ6.9 (1 H, br, s) 5.0 (1H, br, s) 4.24 (1H, q, J=7.2 Hz) 2.79 (3H, s) 1.40 (3H, d, J=7.2 Hz)].

EXAMPLE 11

Preparation of N-Bts-(S)-proline

Yield, 97%, crystallized from hot chloroform/hexane; analytical tic on silica gel, 1:20 AcOH/EtOAc, $R_f$=0.51 . Pure material was obtained by crystallization from chloroform [mp 153.5–155° C., dec; $[\alpha]_D^{25}$−110 (c=2.4, EtOH); molecular ion calcd for $C_{12}H_{13}N_2O_4S_2$(M+H): 313.03174; found m/e=313.0309, error=3 ppm; IR (KBr, $cm^{-1}$) 1714, C=O; 300 MHz NMR ($CDCl_3$, ppm)δ11.21 (1 H, br, s) 8.21–8.18 (1H, m) 8.01–7.98 (1 H, m) 7.66–7.55 (2H, m) 4.76 (1 H, dd, J=7.9, 4.3 Hz) 3.82–3.74 (1H, m) 3.67–3.59 (1H, m) 2.30–1.89 (4H, m)].

EXAMPLE 12

Preparation of N-Ths-(S)-proline

Yield, 94%, crystallized from hot EtOAc with hexane; analytical TLC on silica gel, 1:20 AcOH/EtOAc, $R_f$=0.37. Pure material was obtained by crystallization from EtOAc/hexane [mp 109–110° C.; $[\alpha]_D^{25}$ $^{-112}$ (c=2.3, EtOH); molecular ion calcd for $C_8H_{12}N_3O_4S_2$(M+H): 278.02701; found m/e=278.0266, error=1 ppm; IR (KBr, $cm_{-1}$) 1726, C=O; 300 MHz NMR ($CDCl_3$, ppm) δ10.08 (1H, br, s) 4.67 (1H, dd, J=8.7, 3.6 Hz) 3.83–3.79 (1H, m) 3.68–3.58 (1H, m) 2.89 (3H, s) 2.47–2.31 (1H, m) 2.29–1.97 (3H, m)].

EXAMPLE 13

Preparation of $N_\alpha$-Bts-(S)-tryptophan

Yield, 96% after solvent removal, thick oil (>95% pure by NMR assay); analytical TLC on silica gel, 1:20 AcOH/EtOAc, $R_f$=0.60; [$[\alpha]_D^{25}$ −49.7 (c=2.5, EtOH); molecular ion calcd for $C_{18}H_{16},N_3O_4S_2$ (M+H): 402.05829; found m/e=402.0578, error=1 ppm; IR (KBr, $cm^{-1}$) 3415, N-H; 3284, N-H; 1724, C=O; 300 MHz NMR (DMSO-$d_6$, ppm) δ12.8 (1H, br, s) 10.75 (1H, d, J=1.8 Hz) 9.3 (1H, br, s) 8.19–8.11 (1H, m) 8.10–8.02 (1H, m) 7.66–7.55 (2H, m) 7.46–7.44 (1H, m) 7.21–7.18 (1H, m) 7.12 (1H, d, J=2.6 Hz) 7.01–6.90 (2H, m) 4.28 (1H, dd, J=6.0, 8.3 Hz) 3.18 (1H, dd, J=6.01 14.4 Hz) 2.97 (1H, dd, J=8.31 14.4 Hz)].

EXAMPLE 14

Preparation of N-Bts-(S)-tyrosine

A mixture of (S)-tyrosine (Aldrich, 6.0 g, 33.3 mmol) and N,O-bis(trimethylsilyl)acetamide (Aldrich, 13.5 g, 66.6 mmol) in 50 mL anhydrous acetonitrile was stirred under reflux for 1 h to give a homogenous solution. The stirring was continued for 1 more hour, and the mixture was cooled to room temperature and concentrated by aspirator (hexane in the trap). The residue was dissolved in 100 mL anhydrous $CH_2Cl_2$, the solution cooled to 0° C., and BtsCl (1) (7.8 g, 33.3 mmol) in 60 mL anhydrous $CH_2Cl_2$ was added gradually by cannula over 40 min. Simultaneously, pyridine (2.6 g, 33.3 mmol) was added dropwise. The resulting mixture was stirred for 14 h and was then concentrated (aspirator). To the concentrated residue was added successively 50 mL EtOH, 100 mL $H_2O$, and 40 mL 15% $KHSO_4$. The resulting mixture was stirred for 6 h at room temperature and extracted by EtOAc (3×60 mL). The combined organic layers were washed with brine, dried over $Na_2SO_4$ and concentrated (aspirator) to give the crude product as a yellow solid. Pure material (9.1 g, 72% yield, two crops) was obtained by crystalization from EtOH/$H_2O$ [mp 168–170° C., dec; $[\alpha]_D^{25\ -1.8}$ (c=1.3, EtOH); analytical TLC on silica gel, 20:10:1 EtOAc/hexane/HOAc, $R_f$=0.72; molecular ion calcd for $C_{16}H_{15}N_2O_5S_2$(M+H): 379.0422; HRFABfound m/e=379.0415, error=2 ppm; IR ($CHCl_3$, $cm^{-1}$) 3336, N-H; 3598, H; 1731, C=O; 300 MHz NMR ($CD_3CN$, ppm) δ8.1–8.0 (2H, m) 7.7–7.6 (2H, m) 6.96 (2H, d, J=8.7 Hz) 6.66 (1H, d, J=9.0 Hz) 6.53 (2H, d, J=8.7 Hz) 4.38 (1H, ddd, J=9.0, 8.7, 4.9 Hz) 3.05 (1H, dd, J=13.9, 4.9 Hz) 2.81 (1H, dd, J=13.9, 8.7 Hz)].

EXAMPLE 15

Preparation of N,O-Bis-Ths-(S)tyrosine

The standard procedure was modified to use 3.4 equiv of ThsCl, the reaction mixture was acidified, the white precipitate was collected, dried, and crystallized from EtOH/$H_2O$ to give 90% of the product; analytical TLC on silica gel, 4:1:1 BuOH/AcOH/water, $R_f$=0.55. Pure material was obtained by crystallization from EtOH/$H_2O$[mp 214–21 5 ° C., dec; $[\alpha]_{D25}$–11.7 (c=2.0, DMF); molecular ion calcd for $C_{15}H_{16}N_5O_7S_4$ 505.99338; found m/e=505.9933, error=0 ppm; IR (KBr, $cm_{-1}$) 3107, N-H; 1736, C=O; 300 MHz NMR (DMSO-$d_6$, ppm)δ13.1 (1H, br, s) 9.4 (1H, br, s) 7.27–7.24 (2H, m) 7.08–7.04 (2H, m) 4.09 (1H, dd, J=10.2, 4.6 Hz) 3.09 (1H, dd, J=13.8, 4.6 Hz) 2.86 (3H, s) 2.76 (1H, dd, J=13.87 10.2 Hz) 2.74 (3H, s)].

Example 16

Preparation of $N_\alpha$,$N_\epsilon$-Bis-Ths-(S)-lysine

The standard procedure was modified to use 3.3 equiv ThsCl. Solvent removal gave the product as a solid in 89% yield, >95% pure by NMR assay; analytical TLC on silica gel, 4:1–1 BuOH/AcOH/water, $R_f$=0.55. Pure material was obtained by crystallization from acetonitrile [mp 171–172° C., dec; $[\alpha]_D^{25}$ +4.4 (c=2.1, DMF); molecular ion calcd for $C_{12}H_{19}N_6O_6S_4$(M+H): 471.02508; found m/e=471.0241, error=2ppm; IR (KBr, $cm^{-1}$) 3284, N-H; 3255, N-H; 1732, C=O; 300 MHz NMR (DMSO-$d_6$, ppm)δ12.8 (1H, br, s) 9.2 (1H, br, s) 8.73 (1H, br, s) 3.90–3.85 (1H, m) 3.00–2.94 (2H, m) 2.81 (3H, s) 2.79 (3H, s) 1.72–1.17 (6H, m)].

EXAMPLE 17

Preparation of N-Ths-(S)-serine

The standard procedure was modified because the product is water soluble. Thus, the reaction mixture was acidified and evaporated to 1/10 of the volume (aspirator) and extracted with EtOAc. After drying and concentration as usual, the resulting oil was crystallized from ether to give the product in 74% yield; analytical TLC on silica gel, 4:1:1 nBuOH/AcOH/water, $R_f$=0.33. Pure material was obtained by crystallization from chloroform/acetone [mp 138.5–139.5 ° C., dec; $[\alpha]_D^{25}$ +24.5 (c=2.1, EtOH); molecular ion calcd for $C_6H_{10}N_3O_5S_2$ (M+H): 268.00622; found m/e=268.0069, error=2 ppm; IR (KBr, $cm^{-1}$) 3290, O—H; 3132, N-H; 1747, C=O; 300 MHz NMR ($CD_3CN$, ppm) δ5.6 (3H, br, s) 4.25 (1H, dd, J=4.0, 4.0 Hz) 3.86 (1H, ABX, J=11.51 4.0 Hz) 3.77 (1H, ABX, J=11.5, 4.0 Hz) 2.79 (3H, s)].

Deprotection of Protected Amino Acids

EXAMPLE 18

Deprotection of N-Bts-(S)-phenylglycine

Zn/HOAc-Ethanol Method: To a solution of N-Bts-(S)-phenylglycine (0.18 g, 0.52 mmol) in 5 mL of EtOH was added Zn powder (Mallinckrodt, 0.56 g, 8.5 mmol) and AcOH (0.70 mL, 12.2 mmol). After the reaction mixture was stirred at RT for 14 h, TLC analysis indicated complete consumption of the starting material. The reaction was quenched with cold saturated oxalic acid (10 mL). The unreacted Zn was removed by filtering the finely divided suspension through Celite™, and the Celite™ cake was washed with 10 mL of saturated oxalic acid. The neutral side product (4) was removed by washing with ether (2×15mL), and the aqueous layer was loaded onto a strongly acidic ion exchange column (Dowex 50X8–100, 50–100 mesh, 0.9×15 cm). After washing with 50 mL deionized water, the column was eluted with 75 mL 10% $NH_4OH$. The ammonia eluent was collected and evaporated to dryness (rotary evaporator) and dried under vacuum to give the product phenylglycine as white plates (78 mg, 100%). The enantiomeric purity was established as 99.9% ee by HPLC analysis of the 3,5-dinitrobenzoyl derivative [prepared from amino acid (45 mg)+3,5-dinitrobenzoyl chloride (72 mg)+propylene oxide (0.1 mL), THF (3 mL), RT, 1 h] on a Regis S-N1N-NAPHTHYLLEU column, 50% methanol/50% 6 mM $KH_2PO_4$; flow rate=0.7 mL/min; $t_R$=9.5 min for the (R)-isomer, $t_R$=15.7 min for the (S)-isomer.

$H_3PO_2$ Method: To a stirred and refluxed solution of N-Bts-(S)-Phg (248 mg, 0.712 mmol) in distilled THF (2 mL) under a slow nitrogen stream was slowly added 50% $H_3PO_2$ (Aldrich, 1.5 mL, 14.5 mmol) dropwise over 2 h. After cooling to rt, EtOAc (10 mL) was added and the organic phase was extracted with 3×5 mL water. The combined aqueous phase was loaded onto a 1×15 cm column of Dowex 5×8–100 resin (pretreated with 50 mL $H_2O$ 50 mL 1 M NaOH, 50 mL $H_2O$, 50 mL 10% HCl, and 50 mL $H_2O$). The loaded column was washed with 100 mL water, and then was eluted with 75 mL of 10% aqueous ammonia solution. The ammonia eluent was evaporated and the residue was dried under vacuum to afford 100 mg (93%) white plates of phenylglycine. Assay as described above revealed 99.5% ee.

EXAMPLE 19

Deprotection of N-Ths-(S)-phenylglycine

Zn-HOAc/Ethanol Method: To a solution of N-Ths-(S)-phenylglycine (0.10 g; 0.32 mmol) in 3 mL of EtOH was added Zn powder (Mallinckrodt, 0.32 g, 4.9 mmol) and AcOH (0.40 mL, 7.0 mmol). After the reaction mixture was stirred at RT for 5.5 h, TLC analysis indicated complete consumption of the starting material. The reaction was quenched with cold saturated oxalic acid (10 mL). The unreacted Zn was removed by filtering through Celite™, and the Celitel™ cake was washed with 10 mL of saturated oxalic acid. The neutral side product was removed by washing with ether (2×15 mL), and the aqueous layer was loaded onto a strongly acidic ion exchange column (Dowex 50X8–400, 200–400 mesh, 4 g). After washing with 50 mL deionized water, the column was eluted with 10% $NH_4OH$. The ninhydrin active fractions were collected and evaporated to dryness (rotary evaporator). The residue was dissolved in 10 mL of deionized water and concentrated again to dryness. The solid thus obtained was washed with ether (3×5 mL) and dried under vacuum over $P_2O_5$ to give the product phenylglycine (48 mg, 100%). The enantiomeric purity was established as >99.8% ee by HPLC analysis of the 3,5-dinitrobenzoyl derivative [prepared from amino acid (5 mg)+3,5-dinitrobenzoyl chloride (5 mg)+propylene oxide (0.2 mL), THF (2 mL), RT, 45 min] on a Regis, S-N 1N-NAPHTHYLLEU column, 65% methanol/35% 10 mM $KH_2PO_4$, pH=6.86; flow rate=0.6 mL/min; $t_R$=10–9 min for the (R)-isomer, $t_R$=15.5 min for the (S)-isomer.

Zn-THF/HCl Method: To a solution of N-Ths-(S)-phenylglycine (0.10 g, 0.32 mmol) in 3 mL of THF was added Zn powder (0.30 mg, 4.6 mmol) and conc HCl (0.20 mL, 2.4 mmol). After the reaction mixture was stirred at RT for 6 h, TLC analysis indicated complete consumption of the starting material, and the reaction was quenched with cold saturated oxalic acid (10 mL). The unreacted Zn was removed by filtering through Celite™, and the Celite™ cake was washed with 10 mL of saturated oxalic acid. The product was purified and the enantiomeric purity was assayed as described above, >99.8% ee.

Aluminum Amalgam Method: To a solution of N-Ths-(S)-phenylglycine (0.10 g, 0.32 mmol) in 3 mL of THF was added Al (aluminum foil, polished with sandpaper and cut to small pieces; 86 mg, 3.1 mmol), a few crystals of $HgCl_2$, and $H_2O$(0.12 mL, 6.7 mmol). After the reaction mixture was stirred at RT for 3.5 h, TLC analysis indicated complete consumption of the starting material. The product was purified and assayed as described above, >99.8% ee.

HCl-Methanol Method: N-Ths-(S)-phenylglycine (5.3 mg, 0.017 mmol) was dissolved in 0.5 mL of MeOH and 1 mL of 2 M HCl. After the reaction mixture was stirred at 65° C. for 30 h, TLC analysis indicated complete consumption of the starting material. The neutral side product (2-hydroxy-5-methyl-1,3,4thiadiazole) was removed by washing with $Et_2O$ (2×5 mL), the aqueous solution was then concentrated (aspirator), and the solid residue was dried over $P_2O_5$ to give pure phenylglycine (NMR assay) as its hydrogen chloride salt. The enantiomeric purity was established as 99.6% ee by HPLC analysis of the 3,5-dinitrobenzoyl derivative as described above.

EXAMPLE 20

Deprotection of N-Ths-(S)-phenylalanine.

Zn-HOAc/Ethanol Method: To a solution of N-Ths-(S)-phenylalanine (0.10 g, 0.30 mmol) in 3 mL of EtOH was added Zn powder (Mallinckrodt, 0.30 g, 4.6 mmol) and AcOH (0.35 mL, 6.1 mmol). After the reaction mixture was stirred at RT for 5.5 h, TLC analysis indicated complete consumption of the starting material. The reaction was then quenched with cold saturated oxalic acid (10 mL). The unreacted Zn was removed by filtering through Celite™, and the Celite™ cake was washed with 10 mL of saturated oxalic acid. The neutral methylthiadiazole side product was removed by washing with ether (2×15 mL), and the aqueous layer was loaded onto a strongly acidic ion exchange column (Dowex 50X8–400, 200–400 mesh, 6 g). After washing with 100 mL deionized water, the column was eluted with 10% $NH_4OH$. The ninhydrin active fractions were collected and evaporated to dryness (rotary evaporator). The residue was dissolved in 10 mL of deionized water and concentrated again to dryness. The solid thus obtained was washed with ether (3×5 mL) and dried under vacuum over $P_2O$, to give spectroscopically pure phenylalanine (48 mg, 96%). The NMR spectral data ($D_2O$) matched those of a commercial sample (Aldrich). The enantiomeric purity was established as 99.6% ee by HPLC analysis of the 3,5-dinitrobenzoyl derivative [amino acid (5 mg)+3,5-dinitrobenzoyl chloride (5 mg)+propylene oxide (0.2 mL), THF (2 mL), RT, 45 min] on a Regis, S-N1N-NAPHTHYLLEU column, 65% methanol/35% 10 mM $KH_2PO_4$, pH=6.86; flow rate=0.6 mL/min; $t_R$=6.9 min for the (R)isomer; $t_R$=15.9 min for the (S)-isomer. The same assay procedure was applied to the commercial starting material, and it was also found to be 99.6% ee.

Aluminum Amalgam Method: To a solution of N-Ths-(S)-phenylalanine (38 mg, 0.11 mmol) in 5 mL of THF was added Al (aluminum foil, polished with sandpaper and cut to small pieces; 50 mg, 1.8 mmol), a few crystals of $HgCl_2$, and $H_2O$(0.10 mL, 5.5 mmol). After the reaction mixture was stirred at RT for 1 h, TLC analysis indicated complete consumption of the starting material. The reaction was then quenched with cold saturated oxalic acid (10 mL). The unreacted Al was removed by filtering through Celite™, and the Celite™ cake was washed with 10 mL of saturated oxalic acid. Purification and assay as above established the same ee (99.6%) as in the commercial starting material.

Coupling Reactions-Preparation of Protected Dipeptides

EXAMPLE 21

Preparation of N-Bts-(S)-Phg-(S)-Ala-OMe (7*a*)

To a suspension of N-Bts-(S)-Phg (0.056 g, 0. 161 mmol, 99.9% ee) in 2 mL anhydrous $CH_2Cl_2$ was added $SOCl_2$ (0.057 g, 0.482 mmol) in one portion. The reaction mixture was refluxed in a 50–60° C. oil bath for 40 min to give a homogenous solution. Refluxing was continued for another hour, and the reaction mixture was then cooled to room temperature, and concentrated (aspirator with hexane in the trap). The oily residue was dissolved in 3 mL anhydrous benzene and the solution was concentrated (aspirator) and placed under vacuum for 30 min to remove residual $SOCl_2$, resulting in a residue of N-Bts-(S)-Phg-Cl.

To a cooled (0–5° C.), vigorously stirred mixture of (S)-Ala-OMe.HCl 6*a*) (Aldrich, 0.022 g, 0.161 mmol, 99.6% ee) and $Na_2CO_3$ (0.043 g, 0.402 mmol) in 3 mL $H_2O$and 3 mL $CHCl_3$ was added N-Bts-(S)Phg-Cl from above in 3 mL anhydrous $CH_2Cl_2$ in portions over 1 min by pipette. The resulting solution was stirred for 40 min and was then acidified with 1 N HCl to pH<2. The mixture was partitioned between $CHCl_3$ and $H_2O$. The organic layer was separated and the aqeous layer was extracted by ether (3×10 mL). The combined organic layer was washed with brine, dried over $Na_2SO_4$, concentrated (aspirator) and kept under vacuum for 30 min to give the desired product (0.066 g, 95% yield) which showed no impurities by TLC or $^1H$ NMR assay.

A portion of the crude product was dissolved in $CDCl_3$, and the resulting solution was subjected to NMR analysis.

The $^{1}H$ NMR methyl signal of the ester group for the R,S-isomer (**8*a*) and S,S-isomer (7*a*) was observed at δ3.705 and 3.633 ppm, respectively. By comparing the $^{13}C$ satellite peaks of the major (S,S) isomer (7*a*), the amount of minor (R,S) isomer (8*a*) was determined as 0.15%. A comparable amount of (8*a*) prepared separately was gradually added to the above solution in order to confirm the chemical shift and the assay of the minor isomer by observing the increse of the corresponding proton signal. The de of N-Bts-(S)-Phg-(S)-Ala-OMe (7*a***) was thus established as 99.7%. The product could be further purified by recrystallization from EtOAc/hexane [mp 214–216° C.; $[\alpha]_D^{25}$ +140 (c=0.4, $CH_2Cl_2$); analytical TLC on silica gel, 1:1 EtOAc/hexane, $R_f$=0.3; molecular ion calcd for $C_{19}H_{20}N_3O_5S_2$ (M+H): 434.0844; HRFAB found m/e=434.0851, error=2 ppm; IR ($HCCl_3$, $cm^{-1}$) 3683, N-H; 1685, C=0; 300 MHz NMR ($CDCl_3$, ppm) δ8.1–8.0 (1H, br d, J=8.2 Hz) 8.0–7.9 (1H, br, d, J=7.8 Hz) 7.6–7.5 (2H, m) 7.3–7.2 (5H, m) 6.59 (1H, d, J=6.6 Hz) 6.24 (1H, d, J=6.6 Hz) 5.31 (1H, d, J=6.2 Hz) 4.39 (1H, qd, J=7.4, 6.2 Hz) 3.63 (3H, s) 1.25 (3H, d, J=7.4 Hz)].

EXAMPLE 22

Preparation of N-Bts-(R)-Phg-(S)-Ala-OMe (**8*a***)

The same procedure was used as desribed for the (S,S) isomer, above, starting with 0.489 g of N-Bts-(R)-Phg (from R-phenylglycine, 99.2% ee) and 0.176 g of (S)-Ala-OMe-HCl (Aldrich; 99.6% ee). By comparing the $^{13}C$ satelite peaks of the major (R,S) isomer (**8*a*), the amount of minor (S,S) isomer (7*a*) was determined to be 0.3%. A comparable amount of (7*a*) from above was gradually added to confirm the chemical shift of the minor isomer. The de of Bts-(R)-Phg-(S)-Ala-OMe (8*a*) was thus established as 99.4%. The crude material was purified by flash chromatography (silica gel 2×4cm; 1:1 EtOAc/hexane; 5 mL/min; 15 mL/tube) #23–47 tubes were collected for the product to give 0.494 g (87%) of material that was >98% pure by NMR assay; analytical TLC on silica gel, 1:1 EtOAc/hexane, $R_f$=0.3. Pure (8*a***) was obtained by crystallization from ethyl acetate/chloroform [mp 196–198° C.; $[\alpha]_D^{25}$ +130 (c=1.0, $CHCl_3$); molecular ion calcd for $C_{19}H_{20}N_3O_5S_2$(M+H): 434.0844; HRFAB found m/e=434.0848, error=1 ppm; IR ($CHCl_3$, $cm^{-1}$) 3684, N-H; 1741, C=O; 300 MHz NMR ($CDCl_{31}$, ppm) δ8.07 (1H, dd, J=8.9, 1.6 Hz) 7.91 (1H, dd, J=7.0, 2.0 Hz) 7.6–7.5 (2H, m) 7.3–7.1 (5H, m) 6.59 (1H, d, J=5.8 Hz) 6.37 (1H, d, J=7.4 Hz) 5.31 (1H, d, J=5.8 Hz) 4.44 (1H, qd, J=7.41 5.8 Hz) 3.71 (3H, s) 1.24 (1H, d, J=7.4 Hz)].

EXAMPLE 23

Preparation of tert-Butyl N-Bts-(S)-phenylglycinyl-(S)-phenylalaninate (N-Bts-(S)-Phg-(S)-Phe-Ot-Bu) (**7*b***)

To a suspension of N-Bts-(S)-Phg (113 mg, 0.324 mmol) in 1 mL of dry $CH_2Cl_2$ under nitrogen, $SOCl_2$ (0.070 mL, 0.960 mmol) was added and the stirred suspension was brought to reflux. After the reaction as stirrred for ca. 2 h, the solid dissolved to give a yellow solution. The solvent was evaporated under reduced pressure, the resulting yellow oil was dissolved in 3 mL of dry toluene, and the solvent evaporated again under diminished pressure to give the acyl chloride as a yellow oil, which was used without further purification in the next step.

To a vigorously stirred mixture of (S)-Phe-Ot-Bu hydrochloride (Bachem, 84 mg, 0.326 mmol), $Na_2CO_3$ (70 mg, 0.66 mmol), and $NaHCO_3$ (89 mg, 1.06 mmol) in 2 mL of water and 2 mL of $CH_2Cl_2$ at 0 to 5° C., a solution of the acid chloride (prepared as described above) in 3 mL of dry $CH_2Cl_2$ was added over 1 min. The tan reaction mixture was stirred for 15 min at 0 to 5 ° C. The aqueous layer was separated and washed with 5 mL of $CH_2Cl_2$. The combined organic phase was successively washed with 10 mL of 0.5% aq. HCl and 10 mL of brine, and then dried ($Na_2SO_4$). Concentration of the yellow solution under reduced pressure afforded the product as tan, fine crystals (185 mg). NMR assay of the crude product (30 mg in 0.6 mL of $CDCl_3$) revealed 0.2% of the R, S-diastereomer (**8*b*) (300 MHz, 64 scans), 99.6% de. Under these conditions, the NMR spectrum clearly displayed the $^{13}C$ satellite peaks of the t-Bu group (1.47, 1.05 ppm) of the S, 20 S-diastereomer (7*b*) and the singlet of the t-Bu group (1.39 ppm) of the R,S diastereomer (8*b*). The crude product was recrystallized from hexane/$CHCl_3$ to give fine white crystals of (7*b***) (160 mg, 89% yield starting from N-Bts-(S)-Phg). Analytical TLC on silica gel, 1:1 EtOAc/hexane, $R_f$=0.52. Pure material was obtained by crystallization from chloroform/ethanol [mp 176–177.5° C., dec; $[\alpha]_D^{25}$ +145 (c=2.2 $CH_2Cl_2$); molecular ion calcd for $C_{28}H_{29}N_3O_5S_2$: 551.15491; found m/e=551.1544; IR (KBr, $cm^{-1}$) 3357, N-H; 3288, N-H; 1726, C=O; 300 MHz NMR ($CDCl_3$, ppm) δ8.07–8.01 (1H, m) 7.91–7.86 (1H, m) 7.56–7.48 (2H, m) 7.25–7.12 (8H, m) 7.07–7.01 (2H, m) 6.77 (1 H, s) 6.27 (1 H, d, J=7.6 Hz) 5.24 (1 H, s) 4.58 (1 H, dt, J=7.6, 6.2 Hz) 2.96 (2H, d, J=6.2 Hz) 1.26 (9H, s)].

EXAMPLE 24

Preparation of tert-Butyl N-Bts-(R)-phenylglycinyl-(S)-phenylalaninate, N-Bts-(R)-Phg-(S)-Phe-Ot-Bu (**8*b***)

To a suspension of N-Bts-(R)-Phg (139 mg, 0.399 mmol; from R-Phg with 99.2% ee) in 1 mL of dry $CH_2Cl_2$ under nitrogen, $SOCl_2$ (0.090 mL, 1.23 mmol) was added, and the stirred suspension was brought to reflux. After the reaction was stirred for ca. 2 h, the solid dissolved to give a yellow solution. The solvent was evaporated under reduced pressure, the resulting yellow oil was dissolved in 2 mL of dry toluene, and the solvent evaporated again under diminished pressure to give the acyl chloride as a yellow oil, which was used without further purification in the next step.

To a vigorously stirred mixture of (S)-Phe-OtBu hydrochloride (**6*b*) (Bachem, 108 mg, 0.419 mmol), $Na_2CO_3$ (95 mg, 0.90 mmol), and $NaHCO_3$ (91 Mg, 108 mmol) in 2 mL of water and 2 mL of $CH_2Cl_2$ at 0 to 5° C., a solution of the acid chloride (prepared as described above) in 2 mL of dry $CH_2Cl_2$ was added over 30 s. The orange-tan reaction mixture was stirred for 15 min at 0 to 5° C. The aqueous layer was separated and washed with 5 mL of $CH_2Cl_2$. The combined organic phase was successively washed with 10 mL of 0.5% aq HCl and 10 mL of brine, and then dried ($Na_2SO_4$). Concentration of the yellow solution under reduced presure afforded the product as yellow, fine crystals (225 mg). NMR assay (300 MHz, 64 scans) of the crude product (32 mg in 0.6 mL of $CDCl_3$,) revealed 0.4% of the S, S-diastereomer (7*b*), 99.2% de. Under these conditions, the NMR spectrum clearly displayed the $^{13}C$ satellite peaks of the t-Bu group (1.60, 1.18 ppm) of the R,S-diastereomer (8*b*) and the singlet of the t-Bu group (1.26 ppm) of the S,S-diastereomer (7*b*), which was proved by addition of 0.10 mg of (7*b*) to the NMR sample. A portion of the crude product 8*b*** (193 mg) was recrystallized from EtOH/$CHCl_3$ to give white needles [171 mg from two crops, 91% yield starting from Bts-(R)-Phg); [mp 190–191° C., dec; [α]D$^2$, −87.5 (c=2.0 $CH_2Cl_2$); analytical TLC on silica gel, 1:1 EtOAc/hexane, Rf=0.51; molecular ion calcd for $C_{28}H_{29}N_3O_5S_2$: 551.15491;found m/e=551.1564, error=3 ppm; IR (KBr, $cm^{-1}$) 3408, N-H; 1724, C=Ol 1651, C=O; 300 MHz NMR ($CDCl_3$, ppm) δ8.09–8.03 (1H, m) 7.91–7.85 (1H, m) 7.57–7.48 (2H, m) 7.27–7.17 (5H, m) 7.12–7.07 (1H, m) 7.02–6.97 (2H, m) 6.78 (1H, br s) 6.61–6.59 (2H, m) 6.13 (1H, d, J=7.7 Hz) 5.27 (1H, s) 4.65 (1H, dt, J=7.7, 5.4 Hz) 2.92 (1H, ABX, J=13.8, 5.4 Hz) 2.86 (1H, ABX, J=13.8, 5.4 Hz) 1.39 (9H, s)].

EXAMPLE 25

Preparation of Methyl a-(N-Bts-(S)-phenylglycinylamido)isobutyrate (N-Bts-(S)-Phg-Aib-OMe) (7*c*)

To a suspension of N-Bts-(S)-Phg (197 mg, 0.565 mmol) in 1 mL of dry $CH_2Cl_2$ under nitrogen, $SOCl_2$ (0.12 mL, 1.65 mmol) was added and the stirred suspension was brought to reflux. After the reaction was stirrred for ca. 2 h, the solid dissolved to give a yellow solution. The solvent was evaporated under reduced pressure, the resulting yellow oil was dissolved in 2 mL of dry toluene, and the solvent evaporated again under diminished pressure to give the acyl chloride as a yellow oil, which was used without further purification in the next step.

To a vigorously stirred mixture of Aib-OMe-HCl (91 mg, 0.592 mmol), $Na_2CO_3$ (132 mg, 1.25 mmol), and $NaHCO_3$ (148 mg, 1.76 mmol) in 2 mL of water and 2 mL of $CH_2Cl_2$ at 0 to 5° C., a solution of the acid chloride (prepared as described above) in 1 mL of dry $CH_2Cl_2$ was added over 30 s. The orange-tan reaction mixture was stirred for 15 min at 0 to 5 ° C. The aqueous layer was separated and washed with 10 mL of $CH_2Cl_2$. The combined organic phase was successively washed with 10 mL 0.5% aq. HCl and 10 mL of brine, and then dried ($Na_2SO_4$). Concentration of the yellow solution under reduced pressure afforded the product as yellow, fine crystals (270 mg). The nantiomeric purity was established as 99.8% ee by HPLC analysis on Daicel Chiralpak AS column (25 cm×4.6 mm I.D.), 60% hexanel 40% EtOH, flow rate 0.9 m/min, $t_R$=6.1 for the (S)-isomer 7c, $t_R$=10.6 for the (R)-isomer (8*c*). The crude product was recrystallized from hexane/$CHCl_3$ to afford the product 7*c* as white crystals ([220 mg, 87% yield starting from N-Bts-(S) Phg), mp 154.5–155.5° C., dec; $[\alpha]_D^{25}$ +140 (c=2.2 $CH_2Cl_2$); analytical TLC on silica gel, 1:1 EtOAc/hexane, $R_f$=0.42; molecular ion calcd for $C_{20}H_{22}N_3O_5S_2$ (M+H): 448.10016; found m/e=448.0998; IR (KBr, $cm^{-1}$) 3384, N-H; 1741, C=O; 1695, C=O; 300 MHz NMR ($CDCl_3$, ppm) δ8.08–7.98 (1H, m) 7.94–7.86 (1H, m) 7.58–7.48 (2H, m) 7.34–7.27 (2H, m) 7.22–7.13 (3H, m) 6.88 (1H, s) 6.59 (1H, s) 5.34 (1H, s) 3.56 (3H, s) 1.320 (3H, s) 1.318 (3H, s)].

EXAMPLE 26

Preparation of Methyl a-(N-Bts-(R)-phenylglycinylamido)isobutyrate (N-Bts-(R)-Phg-Aib-OMe) (8*c*)

To a suspension of N-Bts-(R)-Phg (265 mg, 0.760 mmol; 99.2% ee) in 3 mL of dry $CH_2Cl_2$ under nitrogen, $SOCl1_2$ (0.17 mL, 2.33 mmol) was added, and the stirred suspension was brought to reflux. After the reaction was stirrred for ca. 2 h, the solid dissolved to give a yellow solution. The solvent was evaporated under reduced pressure, the resulting yellow oil was dissolved in 2 mL of dry toluene, and the solvent evaporated again under diminished pressure to give the acyl chloride as a yellow oil, which was used without further purification in the next step.

To a vigorously stirred mixture of Aib-OMe.HCl (121 mg, 0.788 mmol), $Na_2CO_3$ (160 mg, 1.5 mmol), and $NaHCO_3$ (140 mg, 1.6 mmol) in 5 mL of water and 5 mL of $CH_2Cl_2$ at 0 to 5° C., a solution of the acid chloride (prepared as described above) in 5 mL of dry $CH_2Cl_2$ was added over 30 s. The orange-tan reaction mixture was stirred for 15 min at 0 to 5° C. The aqueous layer was separated and washed with 10 mL of $CH_2Cl_2$. The combined organic phase was successively washed with 10 mL 0.5% aq. HCl and 10 mL of brine, and then dried ($Na_2SO_4$). Concentration of the yellow solution under reduced pressure afforded the product as yellow, fine crystals (334 mg, 98% yield). The enantiomeric purity was established as 99.2% ee by HPLC analysis on Daicel Chiralpak AS column (25 cm×4.6 mm I.D,), 60% hexane/ 40% EtOH, flow rate 0.9 mL/min; $t_R$=6.1 for the (S)-isomer 7*c*; $t_R$=10.6 for the (R)-isomer 8*c*. A portion of the crude product (314 mg) was dissolved in 10 mL of hot EtOH. 100 mg of activated carbon was added, the cooled mixture was filtered through Celite™, and the colorless filtrate was concentrated under reduced pressure. The crystalline residue was recrystallized from hexane/$CHCl_3$ to afford the product (8*c*) as white crystals ([292 mg, 91% yield starting from N-Bts-(R)-Phg); mp 154.5–155.5° C., dec; $[\alpha]_{D25}$−136 (c=2.1 $CH_2Cl_2$); analytical TLC on silica gel, 1:1 EtOAc/hexane, $R_f$=0.41; molecular ion calcd for $C_{20}H_{22}N_3O_5S_2$ (M+H): 448.10016; found m/e=448.1008; IR (KBr, $cm^{-1}$) 3384, N-H; 1741; C=O; 1695, C=O; 300 MHz NMR ($CDCl_3$, ppm) δ8.02–7.96 (1 H, m) 7.92–7.87 (1 H, m) 7.57–7.48 (2H, m) 7.34–7.27 (2H, m) 7.19–7.11 (3H, m) 7.03 (1H, br s) 6.70 (1H. s) 5.36 (1H, s) 3.53 (3H, s) 1.31 (3H, s) 1.30 (3H, s)].

EXAMPLE 27

Preparation of N-Ths-(S)-Phg-(S)-Phe-Ot-Bu (9*b*)

A suspension of N-Ths-(S)-Phg (0.31 g, 1.0 mmol) in 10 mL of anhydrous $CH_2Cl_2$ under $N_2$ was treated in the usual way with $SOCl_2$ (0.20 mL, 2.7 mmol). and the mixture was brought to reflux. After the reaction was stirred for 1.25 h, the solid dissolved to give a bright yellow solution. The solvent was evaporated with a $N_2$ stream to give the crude acyl chloride as a yellow crystalline solid. The crystals were dried under vacuum over $P_2O_5$ for 2 h to give spectroscopically pure N-Ths-(S)-Phg-Cl in quantitative yield [1300 MHz NMR ($CDCl_3$, ppm) δ7.44–7.31 (5H, m) 6.39 (1H, br d, J=7.8 Hz) 5.74 (IH, d, J=7.8 Hz) 2.84 (3H, s)].

The N-Ths-(S)-Phg-Cl thus obtained was used without further purification for the preparation of N-Ths-(S)-Phg-(S)-Phe-Ot-Bu (9*b*). Thus, to a vigorously stirred mixture of (S)-Phe-Ot-Bu.HCl 6*b* (Bachem, 0.23 g, 0.90 mmol) in 8 mL of $CHCl_3$ and 8 mL of 5% aq $Na_2CO_3$ was added N-Ths-(S)-Phg-Cl in 8 mL of anhydrous $CH_2Cl_2$ over 30 s. The reaction mixture was stirred for 15 min at RT, and then quenched with 2 M HCl. The pH of the aqueous phase was adjusted to 1, and the mixture was partitioned between 15 mL of $H_2O$ and 15 mL of $CHCl_3$. The organic phase was separated, washed successively with $H_2O$ (3×20 mL) and brine, dried ($Na_2SO_4$), and concentrated (aspirator) to give 460 mg of crude dipeptide product as a yellow crystalline solid.

The R,S-isomer (10*b*) (preparation below) could not be detected beyond the $^{13}C$ satellite detection limit by NMR analysis (300 MHz, 96 scans) of the crude N-Ths-(S)-Phg-(S)-Phe-Ot-Bu (9*b*) (10 mg in 0.6 mL $CDCl_3$). Under these conditions, the NMR spectrum clearly displayed the $^{13}C$ satellite peaks of both the thisyl Me group (δ3.00, 2.56 ppm) and of the t-Bu group (δ1.50, 1.07 ppm) for the S,S-isomer, while neither the signal of the thisyl Me (δ2.80 ppm) nor that of the t-Bu group (δ1.42 ppm) of the R,S-isomer isomer was visible. Addition of authentic R,S-isomer (0.1 mg, preparation below) to the NMR sample gave clear new signals for both the methyl and t-butyl resonances. The de of the crude dipeptide (9*b*) was thus determined as >99.8%. Recrystallization of the crude product from $CHCl_3$/hexane yielded 0.40 g of pure N-Ths-(S)-Phg-(S)-Phe-Ot-Bu. The mother liquor was then chromatographed [preparative layer chromatography (PLC), $SiO_2$, 1:1 EtOAc/hexane] to give another 0.01 g (combined yield 86%) of (9*b*) after recrystallization from $CHCl_3$/hexane [mp 190.5–191.0° C., fine needles; $[\alpha]_D^{25}$ +136 (c=2.4 $CHCl_3$); analytical TLC on silica gel, 1:1 EtOAc/hexane, $R_f$=0.30; HRFAB found for $C_{24}H_{29}N_4O_5S_2$(M+H): 517.1597, error=3 ppm; IR (KBr, $cm^{-1}$) 3351, N-H; 1730, C=O; 1668, C=O; 300 MHz NMR ($CDCl_3$, ppm) δ7.43–7.30 (8H, m) 7.25–7.18 (2H, m) 6.87–6.75 (1H, br) 6.18 (1H, br d, J=7.5 Hz) 5.33 (1H, s) 4.66 (1H, dt, J=7.51 6.0 Hz) 3.12 (2H, d, J=6.0 Hz) 2.82 (3H, s) 1.30 (9H, s)].

EXAMPLE 28

Preparation of N-Ths-(S)-Phg-Aib-OMe (9*c*)

N-Ths-(S)-Phg-Cl was prepared by reacting 77 mg (0.24 mmol) of N-Ths-(S)-Phg with $SOCl_2$ (50/μL, 0.69 mmol) in 4 mL of anhydrous $CH_2Cl_2$ (1 h, reflux). Solvent removal followed by drying under vacuum for 2 h gave spectroscopically pure N-Ths-(S)-Phg-Cl in quantitative yield and the material was used immediately for the preparation of Ths-(S)-Phg-Aib-OMe.

To a vigorously stirred mixture of Aib-OMe.HCl (35 mg, 0.23 mmol, prepared by the procedure of El-Abadelah et al., Heterocyles 32 (1991) 1979, incorporated herein by reference, in 2 mL of $CHCl_3$ and 2 mL of 5% aq. $Na_2CO_3$ was added N-Ths-(S)-Phg-Cl in 1 mL of anhydrous $CH_2Cl_2$ over 15 s. The reaction mixture was stirred for 15 min at RT, and was then quenched with 2 M HCl. The pH of the aqueous phase was adjusted to 1, and the mixture was partitioned between 10 mL of $H_2O$ and 10 mL of $CHCl_3$. The organic phase was separated, washed successively with $H_2O$ (2×10 mL) and brine, dried ($Na_2SO_4$), and concentrated (aspirator). The yellow crystalline solid thus obtained was dried under vacuum to give 66 mg (65%) of spectroscopically pure N-Ths-(S)-Phg-Aib-OMe (9*c*).

A portion of the above material (9.5 mg) and trisl3-(trifluoromethylhydroxymethylene)-(+)-camphorato europium(III) (Eu(tfc)$_3$), (Aldrich, 2.5 mg) were dissolved in 0.6 mL of $CDCl_3$, and the resulting solution was subjected to NMR analysis (300 MHz, 121 scans). No signals belonging to N-Ths-(R)-Phg-Aib-OMe (10*c*) were observed beyond the $^{13}C$ satellite detection limit. Under the same conditions, the NMR spectrum of the above sample after addition of 0.028 mg (0.3%) of authentic N-Ths-(R)-Phg-Aib-OMe (10*c*) (preparation below) clearly displayed a weak new signal for the thisyl Me group (d 2.82 ppm) of (R)-10*c* along with the $^{13}C$ satellite peaks of the thisyl methyl group (δ2.62, 3.06 ppm) of the S-isomer (9*c*). These results indicate that the ee of peptide product is >99.80%. Pure (S)-(9*c*) was obtained by PLC purification ($SiO_2$, 2:1 EtOAc/hexane) to remove colored contaminants, followed by recrystallization from $CH_2Cl_2$/hexane [mp 139.5–140.2° C., microcrystalline; analytical TLC on silica gel, 2:1 EtOAc/hexane, $R_f$=0.28; HRFAB found for $C_{16}H_{21}N_4O_5S_2$ (M+H): 413.0958, error=1 ppm; IR (KBr, $cm^{-1}$) 3144, =C-H; 1742, C=O; 1672, C=O; 300 MHz NMR ($CDCl_3$, ppm) δ7.43 (5H, br s) 6.86–6.72 (1H, br s) 6.51–6.38 (1H, br) 5.35 (1H, s) 3.73 (3H, s) 2.81 (3H, s) 1. 50 (3H, s) 1.49 (3H, s)].

For comparison, the enantiomer of (10*c*) was prepared by the same method from N-Ths-(R)-Phg-Cl (prepared from 77 mg N-Ths-(R)-Phg). Workup as described above gave a yellow crystalline solid (65 mg, 64%), spectroscopically pure N-Ths-(R)-Phg-Aib-OMe. A portion of the material (18 mg) and Eu(tfc)$_3$ (Aldrich, 4.0 mg) were dissolved in 0.6 mL of $CDCl_3$, and the resulting solution was subjected to NMR analysis (300 MHz, 121 scans). No signals belonging to N-Ths-(S)-Phg-Aib-OMe were observed beyond the $^{13}C$ satellite detection limit. The spectrum of the same sample after addition of 0.09 mg (0.5%) of authentic (9*c*) clearly displayed the $^{13}C$ satellite peaks of the thisyl Me group (δ3.02, 2.58 ppm) of the R-isomer along with a new weak signal (δ2.84 ppm), which corresponds to the shifted thisyl Me of the (9*c*). These results indicate that the ee of product is >99.8%. The NMR data were identical to those given above for (10*c*).

EXAMPLE 29

Preparation of N-Ths-(S)-Phe-(S)-Ala-OMe (13)

The N-Ths-(S)-Phe-Cl was prepared as described above. Thus, to a suspension of N-Ths-(S)-Phe (0.16 g, 0.5 mmol) in 3 mL of anhydrous $CH_2Cl_2$ under $N_2$ was added $SOCl_2$ (0.1 1 mL, 1.5 mmol), and the mixture was brought to reflux. After the reaction was stirred for 30 min, the solid all dissolved. The resulting light yellow solution was stirred for another 15 min to insure complete reaction, and the solvent was evaporated with a $N_2$ stream to give the crude acyl chloride as a white crystalline solid. The crystals were dried under vacuum over $P_2O_5$ for 2 h to give spectroscopically pure N-Ths-(S)-Phe-Cl in quantitative yield, which was used for the preparation of Ths-(S)-Phe-(S)-Ala-OMe without further purification.

To a vigorously stirred mixture of (S)-Ala-OMe.HCl (Aldrich, 63 mg, 0.45 mmol) in 4 mL of $CHCl_3$ and 4 mL of 5% aq $Na_2CO_3$ was added N-Ths-(S)-Phe-Cl (prepared as described above) in 4 mL of anhydrous $CH_2Cl_2$ over 30 s. The reaction mixture was stirred for 15 min at RT, and then quenched with 2 M HCl. The pH of the aqueous phase was adjusted to 1, and the mixture was partitioned between 10 mL of $H_2O$ and 10 mL of $CHCl_3$. The organic phase was separated, and was washed successively with $H_2O$ (2×15 mL) and brine, dried ($Na_2SO_4$), and concentrated (aspirator) to give 146 mg of crude product as a solid.

The NMR spectrum of the crude N-Ths-(S)-Phe-(S)-Ala-OMe (13) (22 mg in 0.6 mL of $CDCl_3$, 300 MHz, 96 scans) displayed a set of weak signals (δ1.31 ppm, d, J=7.2 Hz) for the alanine $CH_3$ group in addition to the major signal (δ1.38 ppm, d, J=7.2 Hz). The minor signal was confirmed to be that of the S,R-isomer by comparison with the spectrum of an authentic mixture, prepared below. The de was thus established as 99.6% by integrating the above weak signals and the $_{13}C$ satellite peaks (δ1.15 ppm, d, J=7.0 Hz; δ1.58 ppm, d, J=7.0 Hz) of the alanine $CH_3$ group of the major diastereomer.

Pure (13) (140 mg, 75%, two crops) was obtained by crystallization from $CH_2Cl_2$/hexane [mp 174.0–174.5° C., fine needles; $[\alpha]_D^{25}$ +27.8 (c=1.9 $CHCl_3$; analytical TLC on silica gel, 2:1 EtOAc/hexane, $R_f$=0.40; HRFAB found for $C_{16}H_{21},N_4O_5S_2$ (M+H).-413.0936, error=4ppm; IR (KBr, cm_1) 3349, N-H; 1724, C=0; 1677, C=O; 300 MHz NMR ($CDCl_3$, ppm) δ7.41–7.26 (5H, m) 6.81 (1H, d, J=7.3 Hz) 6.4 (1H, br s) 4.54 (1H, dd, J=6.6, 6.6 Hz) 4.5 (1H, qd, J=7.3, 7.3 Hz) 3.76 (3H, s) 3.2 (2H, ABX, $J_{AB}$=13.9, $J_{AX}$=$J_{BX}$=6.6 Hz) 2.86 (3H, s) 1.38 (3H, d, J=7.3 Hz)].

To prepare the comparison sample, the same procedure was used starting from N-Ths-(S)-Phe and racemic (R,S)-Ala-OMe-HCl. The product (137 mg, 74%, two crops) was obtained by crystallization from $CH_2Cl_2$/hexane as a 1:1 mixture of S,S- and S,R-isomers (mp 131.0–135.0° C., microcrystalline); analytical TLC on silica gel, 2:1 EtOAc/hexane, $R_f$=0.30. IR (KBr, $cm^{-1}$ ) 3246, N-H; 1737, C=O; 1636, C=O; 300 MHz NMR ($CDCl_3$, ppm) δ7.42–7.25 (5H, m) 6.89 (0.5H, br d, J=7.3 Hz) 6.76 (0.5H, br d, J=7.3 Hz) 6.55–6.15 (IH, br) 4.59–4.43 (2H, m) 3.78 (1.5H, s) 3.77 (1.5H, s) 3.33–3.07 (IH, m) 2.86 (3H, s) 1.38 (1.5H, d, J=7.3 Hz) 1.31 (1.5H, d, J=7.3 Hz)].

In a separate experiment, N-Ths-(S)-Phe-Cl was recrystallized from $CH_2Cl_2$/hexane before it was used for the coupling with (S)-Ala-OMe. Thus, following the same procedure described above, 20 mg of purified N-Ths-(S)-Phe-Cl (0.058 mmol) and 7.6 mg (0.055 mmol) of (S)-Ala-OMe.HCl was reacted in 0.5 mL of $CHCl_3$ and 0.5 mL of 5% aq $Na_2CO_3$. After similar workup, the crude dipeptide (16 mg in 0.6 mL $CDCl_3$) was subjected to NMR analysis (300 MHz, 99 scans); the S,R-isomer (13) could not be observed beyond the $^{13}C$ satellite detection limit, which corresponds to a de of >99.8%. The characterization data for (13) prepared in this way were identical to those reported above.

EXAMPLE 30

Preparation of N-Ths-(R)-Phg-(S)-Phe-Ot-Bu (**10*b***)

N-Ths-(R)-Phg-Cl was prepared as described above for the (S) enantiomer. To a vigorously stirred mixture of (S)-Phe-Ot-Bu.HCl (**6*b*) (Bachem. 0.23 g, 0.90 mmol) in 8 mL of $CHCl_3$ and 8 mL of 5% aq $Na_2CO_3$ was added N-Ths-(R)-Phg-Cl in 8 mL of anhydrous $CH_2Cl_2$ over 30 s. The reaction mixture was stirred for 15 min at RT, and then quenched with 2 M HCl. The pH of the aqueous phase was adjusted to 1, and the mixture was partitioned between 15 mL of $H_2O$ and 15 mL of $CHCl_3$. The organic phase was separated, washed successively with $H_2O$(3×20 mL) and brine, dried ($Na_2SO_4$), and concentrated (aspirator) to give 403 mg (87%) of dipeptide product as a yellow crystalline solid, >95% pure by NMR analysis. A portion of the dipeptide then obtained (10 mg) was dissolved in 0.6 mL of $CDCl_3$), and the resulting solution was subjected to NMR analysis (300 MHz, 96 scans). Under these conditions, the thisyl Me signal (δ2.78 ppm) of the S,S-isomer could not be observed beyond the detection limit, while the $^{13}C$ satellite peaks of the thisyl Me (δ2.97, 2.53 ppm) group of the R,S-isomer were clearly visible. The signals of the S,S-isomer were detected after adding 0.05 mg of the authentic S,S-isomer (9*b***) to the NMR sample. These results indicate that the de of the crude N-Ths-(R)-Phg-(S)-Phe-Ot-Bu is >99.8%.

Recrystallization of the crude product from $CHCl_3$/hexane gave 0.26 g of pure N-Ths-(R)-Phg-(S)-Phe-Ot-Bu. The mother liquor was chromatographed to give another 0.12 g (combined yield of **10*b***, 82%) after recrystallization from EtOAc/hexane (analytical TLC on silica gel, 1:1 EtOAcihexane, $R_f$=0.30). Pure material was obtained by crystallization from $CHCl_3$/hexane [mp 194.0–1 95.0° C., needles; HRFAB found for $C_{24}H_{29}N_4O_5S_2$ (M+H): 517.1582, error=0 ppm; IR (KBr, $cm^{-1}$) 3400, N-H; 1718, C=O; 1677, C=O; 300 MHz NMR ($CDCl_3$, ppm) δ7.50–7.30 (5H, m) 7.24–7.16 (1 H, m) 7. 15–7.06 (2H, m) 7.01–6.90 (1H, br) 6.75–6.67 (2H, m) 6.11 (IH, br d, J=7.9 Hz) 5.30 (IH, s) 4.76 (2H, dt, J=7.91 5.6 Hz) 2.96 (2H, d, J=5.6 Hz) 2.80 (3H, s) 1.42 (9H, s)].

Deprotection of Dipeptides

EXAMPLE 31

Bz-(S)-Phg-(S)-Phe-Ot-Bu (**11*b*) from (9*b***) using Zn-HOAc/EtOH

To a solution of N-Ths-(S)-Phg-(S)-Phe-Ot-Bu (**9*b*) (78 mg, 30 0.15 mmol) in 1.5 mL of EtOH and 0.5 mL of THF (added to help dissolve the sulfonamide) was added Zn powder (0.15 g, 2.3 mmol) and AcOH (0.20 mL, 3.5 mmol). After the reaction mixture was stirred at RT overnight, TLC analysis indicated complete consumption of the starting material. The reaction mixture was then partitioned between 10 mL of saturated $NaHCO_3$ and 10 mL of EtOAc. The organic phase was separated and washed successively with saturated $NaHCO_3$ and brine. The EtOAc solution was then dried ($Na_2SO_4$) and concentrated to give the free dipeptide ester (11*a***) (52 mg, 98%) as a pink oil, >95% pure by NMR analysis. The material thus obtained was converted to the title peptide without further purification.

Thus, to a solution of the above free amine in 1 mL of anhydrous $CH_2Cl_2$ was added i-$Pr_2$NEt (35 μL, 0.20 mmol) and BzCl (20 μL, 0.17 mmol). After stirring at RT for 1 h, the reaction mixture was diluted with 5 mL of $CHCl_3$, and the mixture was successively washed with dilute citric acid, $H_2O$, saturated $NaHCO_3$ and brine. The resulting solution was then dried ($Na_2SO_4$) and concentrated to give the benzoyl-protected dipeptide ester (**11*b***) as a crystalline solid. Further drying under vacuum afforded 63 mg (92%) of product.

A portion (34 mg) of the material thus obtained was dissolved in 0.6 mL of $CDCl_3$, and the resulting solution was subjected to NMR analysis (500 MHz, 300 scans). Under these conditions, a trace of the R,S-isomer could be detected by observing the t-butyl singlet at δ1.43 ppm. To establish the chemical shift identity, 0.5% of authentic (**12*b*), prepared below, was added to the above sample. A singlet at 1.43 ppm was clearly observed with >8-fold intensity compared to the contaminant in the sample of (11*b***). The de of the N-benzoyl dipeptide was thus established as >99.8%. Pure material was obtained by PLC purification ($SiO_2$, 10:1 $CH_2Cl_2$/EtOAc) to remove colored contaminants followed by recrystallization from $CH_2Cl_2$/hexane [mp 162.0–162.5° C., colorless needles; analytical TLC on silica gel, 1:1 EtOAc/hexane, $R_f$=0.51; HRFAB found for $C_{28}H_{31}N_2O_4$ (M+H): 459.2284, error=0 ppm;

IR (KBr, $cm^{-1}$) 1731, C=O; 1662, C=O; 1636, C=O; 300 MHz NMR (CDC13, ppm) δ7.97–7.90 (2H, m) 7.65–7.19 (14H, m) 6.34 (1H, br d, J=7.5 Hz) 5.68 (1 H, d, J=6.5 Hz) 4.76 (IH, ddd, J=7.51 6.0, 6.0 Hz) 3.14 (2H, ABX, $J_{AB}$=13.91 $J_{AX}$=$J_{BX}$=6.0 Hz) 1.33 (9H, s)].

EXAMPLE 32

Preparation of Bz-(S)-Phg-(S)-Phe-Ot-Bu (**11*b*) from (9*b*) using $H_3PO_2$ To a solution of (9*b*) (196 mg, 0.379 mmol) in distilled THF (5 mL) at reflux was added 50% $H_3PO_2$ (Aldrich, 0.40 mL, 3.86 mmol) over 2.5 h. A slow stream of air was maintained through the system to prevent buildup of $H_2S$ (apparent by the smell). The colorless solution was cooled, 5 mL of water was added, and the solution was extracted with 10 mL of hexane. The hexane phase was washed with 5 mL of water, 5 mL of saturated aq $NaHCO_3$ was added to the combined aqueous layers, and the resulting emulsion was extracted with 3×5 mL of EtOAc. The combined EtOAc layers were washed with 10 mL of brine, dried ($Na_2SO_4$), and concentrated to give the product (S)-Phg-(S)-Phe-Ot-Bu (11***a*) as a colorless oil (131 mg, 98%). The material was benzoylated and assayed as described above, 95% yield of (11*b*) (99.8% de).

EXAMPLE 33

Preparation of Bz-(R)-Phg-(S)-Phe-Ot-Bu (12*b*) from (10*b*) using Al-Hg To a solution of N-Ths-(R)-Phg-(S)-Phe-Ot-Bu (10*b*) (39 mg, 0.075 mmol) in 1 mL of THF was added Al (aluminum foil, polished with sandpaper and cut to small pieces; 20 mg, 0.074 mmol), a few crystals of $HgCl_2$, and $H_2O$ (35 $\mu$L, 1.9 mmol). After the reaction mixture was stirred at RT overnight, TLC analysis indicated complete consumption of the starting material. The reaction mixture was then partitioned between 10 mL of saturated $NaHCO_3$ and 10 mL of EtOAc. The organic phase was separated, and was washed successively with saturated $NaHCO_3$ and brine. The EtOAc solution was then dried ($Na_2SO_4$) and concentrated (aspirator) to give the free dipeptide ester as an oil, which was used immediately for the ensuing acylation reaction.

To a solution of the above free amine in 1 mL of anhydrous $CH_2Cl_2$ was added i-$Pr_2$NEt (17 $\mu$L, 0.095 mmol) and BzCl (10 $\mu$L, 0.086 mmol). After stirring at RT for 2 h, the reaction mixture was diluted with 4 mL of $CHCl_3$, and the mixture was washed successively with dilute citric acid, $H_2O$, saturated $NaHCO_3$ and brine. The resulting solution was then dried ($Na_2SO_4$), and concentrated to give the crude benzoyl-protected dipeptide ester (12*b*) (34 mg, 99%) as a crystalline solid.

The de of the N-benzoyl dipeptide thus obtained was established as described above by observing the t-butyl signal region with and without 1% of authentic (11*b*) added. In the former spectrum, the contaminant signal of (11*b*) was 20% or less compared to the authentic standard mixture, >99.6% de. Pure (12*b*) was obtained by PLC purification ($SiO_2$, 10:1 $CH_2Cl_2$/EtOAc) to remove colored contaminants followed by recrystallization from $CH_2Cl_2$/hexane [mp 170.0–170.5° C., colorless needles; analytical TLC on silica gel, 1:1 EtOAc/hexane, $R_f$=0.49; HRFAB found for $C_{28}H_{31}N_2O_4$ (M+H): 459.2285, error=0 ppm; IR (KBr, $cm^{-1}$) 1728, C=O; 1666, C=O; 1638, C=O; 300 MHz NMR ($CDCl_3$, ppm) δ7.96–7.88 (2H, m) 7.72 (IH, br d, J=6.0 Hz) 7.63–7.44 (8H, m) 7.27–7.08 (3H, m) 6.81–6.74 (2H, m) 6.22 (1 H. br d, J=7.9 Hz) 5.65 (1 H, d, J=6.0 Hz) 4.86 (1 H, dt, J=7.9, 5.5 Hz) 3.00 (2H, d, J=5.5 Hz) 1.43 (9H, s)].

EXAMPLE 34

Preparation of Bz-(R)-Phg-(S)-Phe-Ot-Bu (12*b*) from Bts-(R)-Phg-(S)-Phe-Ot-Bu (8*b*) using H3PO2

To a stirred and refluxed solution of tert-butyl N-Bts-(R)-phenylglycinyl-(S)-phenylalaninate (73 mg, 0.132 mmol; 99.2% de) in THF (2 mL) under a slow stream of nitrogen, 50% $H_3PO_2$ (0.30 mL, 2.9 mmol) was added dropwise over 2 h. The colorless solution was cooled, 5 mL of water was added, and the solution was extracted with 10 mL of hexane. The hexane phase was washed with 5 mL of water. 5 mL of saturated aq $NaHCO_3$ was added to the combined aqueous layers, and the resulting emulsion was extracted with 3×5 mL of EtOAc. The combined EtOAc layers were washed with 10 mL of brine, dried ($Na_2SO_4$), and concentrated to give the product (R)-Phg-(S)-Phe-Ot-Bu as a colorless oil (46 mg, 98%). The material was benzoylated and assayed as desribed above, 99.2% de.

Preparation of Protected Representative Simple Amines

EXAMPLE 35

Preparation of N-ths-N,N-dibenzyl amine

To a solution of N,N-dibenzylamine (0.80 mL, 4.2 mmol) and $Et_3N$ (1.2 mL, 8.4 mmol) in 25 mL of anhydrous $CH_2Cl_2$ at 0° C. was added ThsCl (1.2 g, 6.0 mmol, prepared and dried as described above) in small portions over 30 min. After the reaction mixture was stirred at 0 OC for 1.5 h and rt for 30 min, the volatiles were removed (aspirator), and the residue was dissolved in 50 mL of EtOAc. The solution was successively washed with $H_2O$, dilute $H_2SO_4$, $H_2O$, dilute $NaHCO_3$, $H_2O$ and brine. The combined aqueous solution was extracted with EtOAc (1×50 mL), and the EtOAc solution was combined, dried ($MgSO_4$) and concentrated (aspirator) to give the crude product as an oil, which solidified upon cooling. Pure material (1.49 g, 99%, two crops) was obtained by recrystallization from chloroform/hexane [mp 67.5–68.5 ° C., colorless prisms; analytical TLC on silica gel, 2:1 EtOAc/hexane, $R_f$=0.68; m/e, M+l, 360.0828, error=4 ppm; IR (KBr, $cm^{-1}$) 3036, =C-H; 1363, S=O; 1164, S=O; 300 MHz NMR ($CDCl_3$, ppm) δ7.4–7.1 (10H, m) 4.56 (4H, s) 2.84 (3H, s)].

EXAMPLE 36

Preparation of N-Ths-trans-2-methyl-3-triphenylmethylaziridine

To a solution of trans-2-methyl-3-triphenylmethylaziridine (Vedejs et al., J. Am. Chem. Soc. 115 (1993) 1607; incorporated herein by reference) (8.5 mg, 0.028 mmol) and $Et_3N$ (8.0 $\mu$L, 0.058 mmol) in 1 mL of anhydrous $CH_2Cl_2$ at 0 OC was added ThsCl (8.5 mg, 0.043 mmol, prepared and dried as described above) in small portions over 5 min. After the reaction mixture was stirred at 0° C for 1.5 h and RT for 30 min, the volatiles were removed by aspirator, and the residue was dissolved in 5 mL of EtOAc. The solution was washed successively with $H_2O$, dilute $H_2SO_4$, $H_2O$, dilute $NaHCO_3$, $H_2O$ and brine, and then was dried ($K_2CO_3$) and concentrated (aspirator) to give the crude product as a solid. Pure material (10 mg, 77%) was obtained by PLC purification ($SiO_2$, 1:2 EtOAc/hexane) followed by recrystallization from ether/hexane [mp 167.0–167.5° C., colorless crystals; analytical TLC on silica gel, 1:2 EtOAc/hexane, $R_f$=0.29; HRFAB found for $C_{25}H_{24}N_3O_2S_2$ (M+H): 462.1307, error=1 ppm; IR (KBr, $cm^{-1}$) 1401, S=O; 1176, S=O; 300 MHz NMR ($CDCl_3$, ppm) δ7.3–7.2 (9H, m) 7.1–6.9 (6H, m) 4.26 (IH, d, J=4.8 Hz) 2.71 (3H, s) 2.60 (I HI qdl J=6.01 4.8 Hz) 1.89 (3H, dl J=6.0 Hz)].

Deprotection of Protected Simple Amines

EXAMPLE 37

Deprotection of N-Ths-trans-2-methyl-3-triphenylmethylaziridine

To a solution of N-Ths-trans-2-methyl-3-triphenylmethylaziridine (7.4 mg, 0.016 mmol) in 0.5 mL of EtOH was added Zn powder (Mallinckrodt, 16 mg, 0.24 mmol) and AcOH (0.10 mL, 1.7 mmol). After stirring at RT for 3 h, the reaction mixture was partitioned between 5 mL of $Et_2O$ and 5 mL of 1 M NaOH. The organic phase was separated, and the aqueous phase was extracted with ether (4×5 mL). The ether solution was combined, dried ($K_2CO_3$) and concentrated (aspirator). The solid residue thus obtained was purified by PLC ($SiO_2$, hexane/EtOAc, 2:1) to give 3.6 mg (75%) of spectroscopically pure aziridine. Its NMR spectrum is identical to that reported in the literature. (See, Vedejs et al., J. Am. Chem. Soc., 115 (1993) 1607).

In summary, the present invention provides heteroarenesulfonyl protecting groups for amines, particularly for the amino groups of amino acids. The protecting groups react readily with amino groups and are deprotected under relatively mild conditions, i.e., mildly acidic or neutral conditions. Amino acids protected with the heteroarenesulfonyl groups of the present invention can be coupled with various amino acid esters to form dipeptides in which racemization is minimal, i.e., the product is >99% enantiomerically pure, or substantially >99% ee.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method for protecting an amino acid, comprising the step of reacting an amino acid with a compound of formula (II), G—$SO_nX$, wherein G is

IV

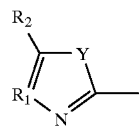

wherein Y is S or O; $R_1$ is C; and $R_1$ and $R_2$, together with the carbon group to which they are bonded, form an unsubstituted six-member aromatic hydrocarbon group;

X is Cl; and n is an integer from 0 to 2, under conditions sufficient to produce an N-protected amino acid.

2. The method of claim 1, wherein said amino acid is an α-amino acid, a β-amino acid, or a γ-amino acid.

3. The method of claim 1, further comprising the step of deprotecting the N-protected amino acid by reacting the N-protected amino acid with a reducing agent under conditions sufficient to produce an unprotected amino acid.

4. The method of claim 3, wherein said reducing agent is selected from the group consisting of Zn/AcOH-EtOH, Al-Hg/ether-$H_2O$, 50% $H_3PO_2$ and Zn/HCl-THF.

5. A method for protecting an amino acid, comprising the step of reacting an amino acid with benzothiazole-2-sulfonyl chloride (BtsCl) under conditions sufficient to produce an N-protected amino acid.

6. The method of claim 5, wherein said amino acid is an α-amino acid, a β-amino acid, or a γ-amino acid.

7. The method of claim 5, further comprising the step of deprotecting the N-protected amino acid by reacting the N-protected amino acid with a reducing agent under conditions sufficient to produce an unprotected amino acid.

8. The method of claim 7, wherein said reducing agent is selected from the group consisting of Zn/AcOH-EtOH, Al-Hg/ether-$H_2O$, 50% $H_3PO_2$ and Zn/HCl-THF.

* * * * *

UNITED STATES PATENT AND TRADEMARK OFFICE

CERTIFICATE OF CORRECTION

PATENT NO : 5,900,427

DATED : May 4, 1999

INVENTOR(S) : Edwin Vedejs, Jiabing Wang, Shouzhong Lin, and Artis Klapars

It is certified that error appears in the above-identified patent and that said Letters Patent is hereby corrected as shown below:

Col. 2, line 6, "α-elimination" should read --β-elimination--.

Col. 3, line 30, "; is a" should read --; Z is a--.

Col. 3, line 67, "fereinafter" should read --hereinafter--.

Col. 6, line 46, "$G-SO_2X$" should read --$G-SO_2$- --.

Col. 9, line 37, "1 5" should read --15--.

Col. 11, line 48, "δ6" should read --δ--.

Col. 13, line 35, "δ6" should read --δ--.

Col. 13, line 46, "$C_{12}H,_{15}N_2O_4S_2$" should read --$C_{12}H_{15}N_2O_4S_2$--.

Col. 14, line 31, "tic" should read --tlc--.

Col. 14, line 47, "$^{-112}$" should read -- -112--.

Col. 14, line 49, "$cm._{1}$" should read -- $cm^{-1}$--.

Col. 15, line 24, "$^{-1.8}$" should read -- -1.8--.

Col. 15, line 41, "214-21 5 ° C.," should read --214-215°C.,--.

Col. 15, line 42, "$[\alpha]_{D25}$-11.7" should read --$[\alpha]_D^{25}$-11.7--.

Col. 15, line 44, "$cm._{1}$" should read -- $cm^{-1}$--.

CERTIFICATE OF CORRECTION

PATENT NO : 5,900,427

Page 2 of 3

DATED : May 4, 1999

INVENTOR(S) : Edwin Vedejs, Jiabing Wang, Shouzhong Lin, and Artis Klapars

It is certified that error appears in the above-identified patent and that said Letters Patent is hereby corrected as shown below:

Col. 15, line 55, "4:1-1" should read --4:1:1--.

Col. 18, line 10, "$P_2O$," should read --$P_2O_5$--.

Col. 19, line 35, "2x4cm" should read --2x14cm--.

Col. 19, line 58, "as" should read --was--.

Col. 20, line 14, "S, 20 S-diastereomer" should read --S,S-diastereomer--.

Col. 20, line 67, "$[\alpha]D^2$," should read --$[\alpha]_D^{25}$--.

Col. 21, line 39, "nantiomeric" should read --enantiomeric--.

Col. 21, line 61, "$SOCl1_2$" should read --$SOCl_2$--.

Col. 22, line 26, "$[\alpha]_{D25}$" should read --$[\alpha]_D^{25}$--.

Col. 22, line 47, "[1300" should read --[300--.

Col. 23, line 59, "(d 2.82" should read --($\delta$ 2.82--.

Col. 24, line 60, "$_{13}C$" should read --$^{13}C$--.

Col. 25, line 65, "194.0-1 95.0°" should read --194.0-195.0°--.

UNITED STATES PATENT AND TRADEMARK OFFICE

CERTIFICATE OF CORRECTION

PATENT NO. : 5,900,427

DATED : May 4, 1999

INVENTOR(S) : Edwin Vedejs, et. al.

It is certified that error appears in the above-identified patent and that said Letters Patent is hereby corrected as shown below:

Col. 25, line 65, "194.0-1 95.0°" should read --194.0-195.0°--.

Signed and Sealed this

Eleventh Day of January, 2000

Attest:

Q. TODD DICKINSON

*Attesting Officer*

*Acting Commissioner of Patents and Trademarks*